(12) United States Patent
Yamada et al.

(10) Patent No.: US 6,337,399 B1
(45) Date of Patent: Jan. 8, 2002

(54) PROCESSES FOR PRODUCING 7-ISOINDOLINEQUINOLONECARBOXYLIC DERIVATIVES AND INTERMEDIATES THEREFOR, SALTS OF 7-ISOINDOLINEQUINOLONECARBOXYLIC ACIDS, HYDRATES THEREOF, AND COMPOSITION CONTAINING THE SAME AS ACTIVE INGREDIENT

(75) Inventors: Minoru Yamada; Shoichi Hamamoto, both of Toyama; Kazuya Hayashi, Uozu; Kazuko Takaoka, Takaoka; Hiroko Matsukura; Minako Yotsuji, both of Toyama; Kenji Yonezawa, Takaoka; Katsuji Ojima, Toyama; Tamotsu Takamatsu, Toyama; Kyoko Taya, Toyama; Hirohiko Yamamoto, Toyama; Taro Kiyoto, Takaoka; Hironori Kotsubo, Toyama, all of (JP)

(73) Assignee: Toyama Chemical Co., Ltd., Tokyo (JP)

( * ) Notice: Subject to any disclaimer, the term of this patent is extended or adjusted under 35 U.S.C. 154(b) by 0 days.

(21) Appl. No.: 09/529,407

(22) PCT Filed: Oct. 27, 1998

(86) PCT No.: PCT/JP98/04854

§ 371 Date: Apr. 26, 2000

§ 102(e) Date: Apr. 26, 2000

(87) PCT Pub. No.: WO99/21849

PCT Pub. Date: May 6, 1999

(30) Foreign Application Priority Data

Oct. 27, 1997 (JP) .............................................. 9-311376
Mar. 20, 1998 (JP) ........................................... 10-092807
May 7, 1998 (JP) ........................................... 10-140586
Aug. 31, 1998 (JP) ........................................... 10-244828
Sep. 8, 1998 (JP) ........................................... 10-253656

(51) Int. Cl.[7] .................... C07D 215/16; C07D 215/20; C07D 207/00
(52) U.S. Cl. ........................ 546/156; 548/405; 514/312
(58) Field of Search ........................ 546/156; 514/312; 548/405

(56) References Cited

U.S. PATENT DOCUMENTS 5,935,952 A    8/1999   Todo et al.
6,025,370 A *  2/2000   Todo

OTHER PUBLICATIONS

CA 127:220579, abstract of WO 9729102, Aug. 1997, Todo.*

* cited by examiner

Primary Examiner—D. Margaret Seaman
(74) Attorney, Agent, or Firm—Oblon, Spivak, McClelland, Maier & Neustadt, P.C.

(57) ABSTRACT

This invention relates to processes for producing a 7-isoindoline-quinolonecarboxylic acid derivative represented by the general formula [1] which is useful as an antibacterial agent, and an intermediate thereof:

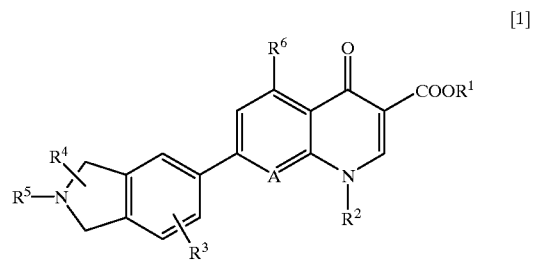

[1]

wherein $R^1$ represents a hydrogen atom or a carboxyl-protecting group; $R^2$ represents a substituted or unsubstituted alkyl, alkenyl, cycloalkyl, aryl or heterocyclic group; $R^3$ represents at least one group selected from hydrogen atom, halogen atoms, substituted or unsubstituted alkyl, alkenyl, cycloalkyl, aryl, alkoxy or alkylthio groups, nitro group, cyano group, acyl groups, protected or unprotected hydroxyl groups and protected or unprotected or substituted or unsubstituted amino groups; $R^4$ represents at least one group selected from hydrogen atom, halogen atoms, substituted or unsubstituted alkyl, alkenyl, cycloalkyl, aralkyl, aryl, alkoxy or alkylthio groups, protected or unprotected hydroxyl or imino groups, protected or unprotected or substituted or unsubstituted amino groups, alkylidene groups, oxo group and groups each forming a cycloalkane group together with the carbon atom to which $R^4$ bonds; $R^5$ represents a hydrogen atom, an amino-protecting group, a substituted or unsubstituted alkyl, cycloalkyl, alkylsulfonyl, arylsulfonyl, acyl or aryl group; $R^6$ represents a hydrogen atom, a halogen atom, a substituted or unsubstituted alkyl, alkoxy or alkylthio group, a protected or unprotected hydroxyl or amino group or a nitro group; and A represents CH or C—$R^7$ in which $R^7$ represents a halogen atom, a substituted or unsubstituted alkyl, alkoxy or alkylthio group or a protected or unprotected hydroxyl group, and to a salt of a 7-isoindoline-quinolonecarboxylic acid represented by the general formula [1], a hydrate thereof and a composition comprising them as an active ingredient.

14 Claims, No Drawings

PROCESSES FOR PRODUCING 7-ISOINDOLINEQUINOLONECARBOXYLIC DERIVATIVES AND INTERMEDIATES THEREFOR, SALTS OF 7-ISOINDOLINEQUINOLONECARBOXYLIC ACIDS, HYDRATES THEREOF, AND COMPOSITION CONTAINING THE SAME AS ACTIVE INGREDIENT

This application is a 371 of PCT/JP98/04854, filed Oct. 27, 1998.

TECHNICAL FIELD

This invention relates to processes for producing a 7-isoindoline-quinolonecarboxylic acid derivative represented by the general formula [1] and its intermediate as well as a salt of 7-isoindoline-quinolonecarboxylic acid derivative represented by the general formula [1], its hydrate and a composition comprising the same as an active ingredient:

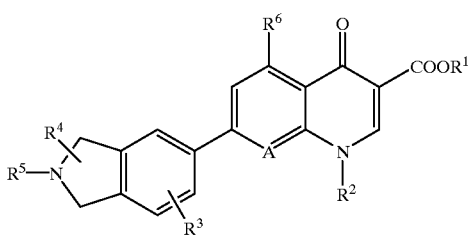

[1]

wherein $R^1$ represents a hydrogen atom or a carboxyl-protecting group; $R^2$ represents a substituted or unsubstituted alkyl, alkenyl, cycloalkyl, aryl or heterocyclic group; $R^3$ represents at least one group selected from hydrogen atom, halogen atoms, substituted or unsubstituted alkyl, alkenyl, cycloalkyl, aryl, alkoxy or alkylthio groups, nitro group, cyano group, acyl groups, protected or unprotected hydroxyl groups and protected or unprotected or substituted or unsubstituted amino groups; $R^4$ represents at least one group selected from hydrogen atom, halogen atoms, substituted or unsubstituted alkyl, alkenyl, cycloalkyl, aralkyl, aryl, alkoxy or alkylthio groups, protected or unprotected hydroxyl or imino groups, protected or unprotected or substituted or unsubstituted amino groups, alkylidene groups, oxo group and groups each forming a cycloalkane ring with the carbon atom to which $R^4$ bonds; $R^5$ represents a hydrogen atom, an amino-protecting group or a substituted or unsubstituted alkyl, cycloalkyl, alkylsulfonyl, arylsulfonyl, acyl or aryl group; $R^6$ represents a hydrogen atom, a halogen atom, a substituted or unsubstituted alkyl, alkoxy or alkylthio group, a protected or unprotected hydroxyl or amino group or a nitro group; and A represents CH or C—$R^7$ in which $R^7$ represents a halogen atom, a substituted or unsubstituted alkyl, alkoxy or alkylthio group or a protected or unprotected hydroxyl group.

BACKGROUND ART

As the process for producing a compound of the general formula [1], there has been known the process described in WO97/29102. That is to say, said publication describes that a compound of the general formula [1] can be produced by subjecting a 5-halogenoisoindoline derivative represented by the following general formula [4] or its salt:

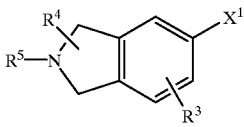

[4]

wherein $R^3$, $R^4$ and $R^5$ have the same meanings as mentioned above and $X^1$ represents a halogen atom, to lithiation or Grignard reaction and thereafter to reaction with a trialkyl borate to form an isoindoline-5-boronic acid derivative represented by the following general formula [2c] or its salt:

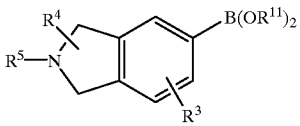

[2c]

wherein $R^3$, $R^4$ and $R^5$ have the same meanings as mentioned above and $R^{11}$ represents a hydrogen atom or an alkyl group; and subsequently reacting the isoindoline-5-boronic acid derivative or its salt with a 7-halogenoquinolonecarboxylic acid represented by the following general formula [3b]:

[3b]

wherein $R^1$, $R^2$, $R^6$ and A have the same meanings as mentioned above and $X^3$ represents a halogen atom, in the presence of a palladium complex such as bis(triphenylphosphine)-palladium(II) chloride, tetrakis(triphenylphosphine)-palladium(0) or the like.

Among the compounds of the general formula [1], (R)-1-cyclopropyl-8-difluoromethoxy-7-(1-methyl-2,3-dihydro-1H-5-isoindolyl)-4-oxo-1,4-dihydro-3-quinoline-carboxylic acid represented by the formula:

(referred to hereinafter as T-3811) is a compound excellent in activity against Gram-positive and Gram-negative bacteria and the development of a process for industrially producing the same has been desired.

Moreover, T-3811 is low in solubility in the vicinity of neutral, so that the enhancement of solubility at a physiologically acceptable pH has been desired.

DISCLOSURE OF THE INVENTION

In order to develop a process for industrially producing a 7-isoindoline-quinolonecarboxylic acid derivative of the general formula [1] including T-3811, the present inventors have diligently made research to find consequently that a coupling reaction between an isoindoline-5-boronic acid derivative represented by the following general formula [2]:

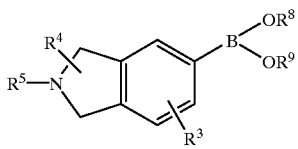

[2]

wherein $R^3$, $R^4$ and $R^5$ have the same meanings as mentioned above and $R^8$ and $R^9$ represent hydrogen atoms or lower alkyl groups or form a ring comprising the boron atom when taken together, and a 7-leaving group-substituted quinolone-carboxylic acid represented by the following general formula [3]:

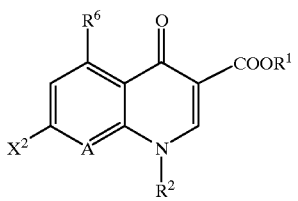

[3]

wherein $R^1$, $R^2$, $R^6$ and A have the same meanings as mentioned above and $X^2$ represents a leaving group, can be easily carried out in the presence of metallic palladium.

Furthermore, it has been found that an isoindoline-5-boronic acid derivative represented by the following general formula [2a]:

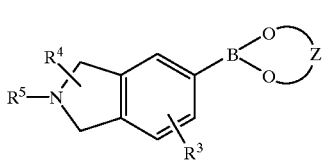

[2a]

wherein $R^3$, $R^4$ and $R^5$ have the same meanings as mentioned above and Z represents an alkylene group can easily be obtained not by the conventional borodation through lithiation or Grignard reaction but by the reaction of a 5-halogenoisoindoline derivative represented by the following general formula [4]:

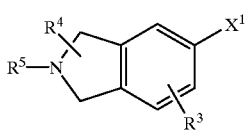

[4]

wherein $R^3$, $R^4$, $R^5$ and $X^1$ have the same meanings as mentioned above, with a dialkoxyborane or an alkoxydiborane in the presence of a palladium catalyst, and further found that the compound of the general formula [2a] can be applied, without being isolated, to the so-called one-pot reaction by which the compound of the general formula [3] is reacted to produce a 7-isoindoline-quinolonecarboxylic acid derivative represented by the general formula [1].

Also, the present inventors have found that a 1-alkylisoindoline-5-boronic acid derivative represented by the following general formula [2b]:

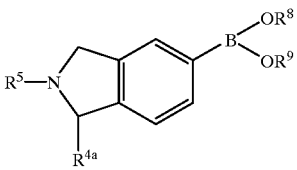

[2b]

wherein $R^{4a}$ represents an alkyl group and $R^5$, $R^8$ and $R^9$ have the same meanings as mentioned above is an excellent intermediate for producing a 7-isoindoline-quinolone-carboxylic acid derivative represented by the following general formula [1a]:

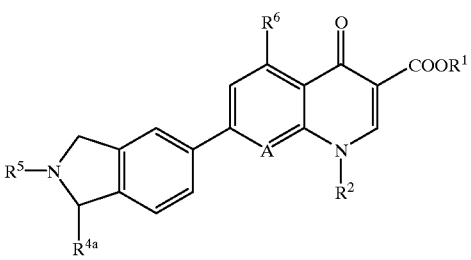

[1a]

wherein $R^{4a}$, $R^1$, $R^2$, $R^5$, $R^6$ and A have the same meanings as mentioned above among the compounds of the general formula [1].

Moreover, it has been found that a 1-alkyl-5-halogenoisoindoline derivative represented by the following general formula [4a]:

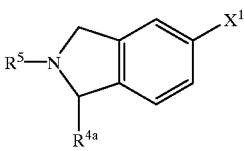

[4a]

wherein $R^{4a}$, $R^5$ and $X^1$ have the same meanings as mentioned above, can be produced by using a 4-halogenobenzylamine derivative as the starting material.

Furthermore, it has been found that as the process for producing a 7-bromo-quinolonecarboxylic acid derivative represented by the following general formula [3a] which is a useful intermediate for producing T-3811:

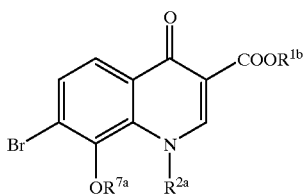

[3a]

wherein $R^{1b}$ represents a carboxyl-protecting group; $R^{7a}$ represents a substituted or unsubstituted alkyl group; and $R^{2a}$ represents a substituted or unsubstituted alkyl, cycloalkyl, aryl or heterocyclic group, a process in which a 2,4-dibromo-3-hydroxybenzoic acid ester is used as the starting material and which is through various intermediates as mentioned hereinafter is an excellent industrial production process.

As mentioned above, the present inventors have diligently made research on 7-isoindoline-quinolone-carboxylic acid derivatives represented by the general formula [1] including T-3811 and intermediates for producing the same and have accomplished this invention.

In addition, the present inventors have examined various salts of T-3811 which have never been known, and have consequently found that among them, methanesulfonate of T-3811 is much higher in solubility at a physiologically acceptable pH than the other salts of T-3811 and further that T-3811 methanesulfonate hydrate has no polymorphism and is good in stability against humidity, and hence, it has a very high usefulness as a composition, particularly as a starting material for preparation, whereby this invention has been accomplished.

In the present specification, unless otherwise specified, the term "halogen atom" means fluorine atom, chlorine atom, bromine atom or iodine atom; the term "alkyl group" means a straight or branched chain $C_{1-10}$ alkyl group, for example, methyl, ethyl, n-propyl, isopropyl, n-butyl, isobutyl, sec-butyl, tert-butyl, pentyl, hexyl, heptyl, octyl or the like; the term "alkenyl group" means a straight or branched chain $C_{2-10}$ alkenyl group, for example, vinyl, allyl, isopropenyl, butenyl, pentenyl, hexenyl, heptenyl, octenyl or the like; the term "alkylidene group" means a straight or branched chain $C_{1-10}$ alkylidene group, for example, methylene, ethylidene, propylidene, isopropylidene, butylidene, hexylidene, octylidene or the like; the term "cycloalkyl group" means a $C_{3-6}$ cycloalkyl group, for example, cyclopropyl, cyclobutyl, cyclopentyl, cyclohexyl or the like; the term "cycloalkane ring" means a $C_{3-6}$ cycloalkane ring, for example, cyclopropane, cyclobutane, cyclopentane, cyclohexane or the like; the term "alkylene group" means a straight or branched chain $C_{1-10}$ alkylene group, for example, ethylene, trimethylene, tetramethylene, 1,2-dimethylethylene, 1,3-dimethyl-trimethylene, 1,1,2,2-tetramethylethylene or the like; the term "alkoxy group" means a straight or branched chain $C_{1-10}$ alkoxy group, for example, methoxy, ethoxy, n-propoxy, isopropoxy, n-butoxy, isobutoxy, sec-butoxy, tert-butoxy, pentyloxy, hexyloxy, heptyloxy, octyloxy or the like; the term "alkoxycarbonyl group" means an alkoxy—CO— group (in which the alkoxy represents the above-mentioned straight or branched chain $C_{1-10}$ alkoxy group), for example, methoxycarbonyl, ethoxycarbonyl, n-propoxycarbonyl, isopropoxycarbonyl, n-butoxycarbonyl, isobutoxycarbonyl, sec-butoxycarbonyl, tert-butoxycarbonyl, pentyloxycarbonyl or the like; the term "alkylamino group" means a straight or branched chain $C_{1-10}$ alkyl group-substituted amino group, for example, methylamino, ethylamino, propylamino, butylamino, pentylamino, hexylamino, dimethylamino, diethylamino, methylethylamino, dipropylamino, dibutylamino, dipentylamino or the like; the term "alkylthio group" means a straight or branched chain $C_{1-10}$ alkylthio group, for example, methylthio, ethylthio, n-propylthio, isopropylthio, n-butylthio, isobutylthio, sec-butylthio, tertbutylthio, pentylthio, hexylthio, heptylthio, octylthio or the like; the term "alkylsulfonyl group" means a straight or branched $C_{1-10}$ alkylsulfonyl group, for example, methylsulfonyl, ethylsulfonyl, n-propylsulfonyl, isopropylsulfonyl, n-butylsulfonyl, isobutylsulfonyl, sec-butylsulfonyl, tert-butylsulfonyl, pentylsulfonyl, hexylsulfonyl, heptylsulfonyl, octylsulfonyl or the like; the term "acyl group" means, for example, a formyl group, a straight or branched chain $C_{2-5}$ alkanoyl group such as acetyl, ethylcarbonyl or the like or an aroyl group such as benzoyl, naphthylcarbonyl or the like; the term "aryl group" means, for example, a phenyl or naphthyl group; the term "arylsulfonyl group" means, for example, a phenylsulfonyl or naphthylsulfonyl group; the term "aralkyl group" means, for example, a benzyl, phenethyl, diphenylmethyl or triphenylmethyl group; the term "heterocyclic group" means a 4-membered, 5-membered or 6-membered ring containing at least one hetero atom selected from oxygen atom, nitrogen atom and sulfur atom as the hetero atom forming the ring or a condensed ring thereof, for example, an oxetanyl, thietanyl, azetidinyl, furyl, pyrrolyl, thienyl, oxazolyl, isoxazolyl, imidazolyl, thiazolyl, isothiazolyl, pyrrolidinyl, benzofuranyl, benzothiazolyl, pyridyl, quinolyl, pyrimidinyl or morpholinyl group.

Moreover, in the present specification, the term "lower" means 1 to 5 carbon atoms, provided that the term "lower" in the term "lower alkenyl" means 2 to 5 carbon atoms.

The protecting groups for amino group, lower alkylamino group and imino group include all conventional groups usable as amino-protecting groups, and there are mentioned, for example, acyl groups such as trichloroethoxycarbonyl, tribromoethoxycarbonyl, benzyloxycarbonyl, p-nitrobenzyloxycarbonyl, o-bromobenzyloxycarbonyl, (mono-, di-, tri-)chloroacetyl, trifluoroacetyl, phenylacetyl, formyl, acetyl, benzoyl, tert-amyloxycarbonyl, tert-butoxycarbonyl, p-methoxybenzyloxycarbonyl, 3,4-dimethoxy-benzyloxycarbonyl, 4-(phenylazo)benzyloxycarbonyl, 2-furfuryloxycarbonyl, diphenylmethoxycarbonyl, 1,1-dimethylpropoxycarbonyl, isopropoxycarbonyl, phthaloyl, succinyl, alanyl, leucyl, 1-adamantyloxycarbonyl, 8-quinolyloxycarbonyl, pivaloyl and the like; ar-lower alkyl groups such as benzyl, diphenylmethyl, trityl and the like; arylthio groups such as 2-nitrophenylthio, 2,4-dinitrophenylthio and the like; alkyl- or aryl-sulfonyl groups such as methanesulfonyl, p-toluenesulfonyl and the like; di-lower alkylamino-lower alkylidene groups such as N,N-dimethylaminomethylene and the like; ar-lower alkylidene groups such as benzylidene, 2-hydroxybenzylidene, 2-hydroxy-5-chlorobenzylidene, 2-hydroxy-1-naphthylmethylene and the like; nitrogen-containing heterocyclic alkylidene groups such as 3-hydroxy-4-pyridylmethylene and the like; cycloalkylidene groups such as cyclohexylidene, 2-ethoxycarbonylcyclohexylidene, 2-ethoxycarbonylcyclopentylidene, 2-acetylcyclohexylidene, 3,3-dimethyl-5-oxycyclohexylidene and the like; diaryl- or di-ar-lower alkyl-phosphoryl groups such as diphenylphosphoryl, dibenzylphosphoryl and the like; oxygen-containing heterocyclic alkyl groups such as 5-methyl-2-oxo-2H-1,3-dioxol-4-yl-methyl and the like; substituted silyl groups such as trimethylsilyl and the like; etc.

The protecting groups for the carboxyl group include all conventional groups usable as carboxyl-protecting groups and there are mentioned, for example, lower alkyl groups such as methyl, ethyl, n-propyl, isopropyl, 1,1-dimethylpropyl, n-butyl, tert-butyl and the like; aryl groups such as phenyl, naphthyl and the like; ar-lower alkyl groups such as benzyl, diphenylmethyl, trityl, p-nitrobenzyl, p-methoxybenzyl, bis(p-methoxy-phenyl)methyl and the like; acyl-lower alkyl groups such as acetylmethyl, benzoylmethyl, p-nitrobenzoylmethyl, p-bromobenzoylmethyl, p-methanesulfonylbenzoylmethyl and the like; oxygen-containing heterocyclic groups such as 2-tetrahydropyranyl, 2-tetrahydrofuranyl and the like; halogeno-lower alkyl groups such as 2,2,2-trichloroethyl and the like; lower alkylsilyl-lower alkyl groups such as 2-(trimethylsilyl)ethyl and the like; acyloxy-lower alkyl groups such as acetoxymethyl, propionyloxymethyl, pivaloyloxymethyl and the like; nitrogen-containing heterocyclic-lower alkyl groups such as phthalimidomethyl, succinimidomethyl and the like; cycloalkyl groups such as cyclohexyl and the like; lower alkoxy-lower alkyl groups such as methoxymethyl, methoxyethoxymethyl, 2-(trimethyl-silyl)ethoxymethyl and the like; ar-lower alkoxy-lower alkyl groups such as benzyloxymethyl and the like; lower alkylthio-lower alkyl groups such as methylthiomethyl, 2-methylthioethyl and the like; arylthio-lower alkyl groups such as phenylthiomethyl and the like; lower alkenyl groups such as 1,1-dimethyl-2-propenyl, 3-methyl-3-butenyl, allyl and the like; substituted silyl groups such as trimethylsilyl, triethylsilyl, triisopropylsilyl, diethylisopropylsilyl, tert-butyldimethylsilyl, tert-butyldiphenylsilyl, diphenylmethylsilyl, tert-butylmethoxyphenylsilyl and the like.

The protecting groups for the hydroxyl group include all conventional groups usable as hydroxyl-protecting groups and there are mentioned, for example, acyl groups such as benzyloxycarbonyl, 4-nitrobenzyloxycarbonyl, 4-bromobenzyloxycarbonyl, 4-methoxybenzyloxycarbonyl, 3,4-dimethoxybenzyloxycarbonyl, methoxycarbonyl, ethoxycarbonyl, tert-butoxycarbonyl, 1,1-dimethylpropoxycarbonyl, isopropoxycarbonyl, isobutyloxycarbonyl, diphenylmethoxycarbonyl, 2,2,2-trichloroethoxycarbonyl, 2,2,2-tribromoethoxycarbonyl, 2-(trimethylsilyl)-ethoxycarbonyl, 2-(phenylsulfonyl)ethoxycarbonyl, 2-(triphenylphosphonio)ethoxycarbonyl, 2-furfuryloxycarbonyl, 1-adamantyloxycarbonyl, vinyloxycarbonyl, allyloxycarbonyl, S-benzylthiocarbonyl, 4-ethoxy-1-naphthyloxycarbonyl, 8-quinolyloxycarbonyl, acetyl, formyl, chloroacetyl, dichloroacetyl, trichloroacetyl, trifluoroacetyl, methoxyacetyl, phenoxyacetyl, pivaloyl, benzoyl and the like; lower alkyl groups such as methyl, tert-butyl, 2,2,2-trichloroethyl, 2-trimethylsilylethyl and the like; lower alkenyl groups such as allyl and the like; ar-lower alkyl groups such as benzyl, p-methoxybenzyl, 3,4-dimethoxybenzyl, diphenylmethyl, trityl and the like; oxygen-containing and sulfur-containing heterocyclic groups such as tetrahydrofuryl, tetrahydropyranyl, tetrahydrothio-pyranyl and the like; lower alkoxy- and lower alkylthiolower alkyl groups such as methoxymethyl, methylthiomethyl, benzyloxymethyl, 2-methoxyethoxymethyl, 2,2,2-trichloroethoxymethyl, 2-(trimethylsilyl)ethoxymethyl, 1-ethoxyethyl, 1-methyl-1-methoxyethyl and the like; lower alkyl- and aryl-sulfonyl groups such as methanesulfonyl, p-toluenesulfonyl and the like; substituted silyl groups such as trimethylsilyl, triethylsilyl, triisopropylsilyl, diethylisopropylsilyl, tert-butyldimethylsilyl, tert-butyldiphenylsilyl, diphenylmethylsilyl, tert-butylmethoxy-phenylsilyl and the like; etc.

The substituent of the alkyl, alkenyl, cycloalkyl, aryl or heterocyclic group for $R^2$; the substituent of the alkyl, alkenyl, cycloalkyl, aryl, alkoxy, alkylthio or amino group for $R^3$; the substituent of the alkyl, alkenyl, cycloalkyl, aralkyl, aryl, alkoxy, alkylthio or amino group for $R^4$; the substituent of the alkyl, cycloalkyl, alkyl-sulfonyl, arylsulfonyl, acyl or aryl group for $R^5$; the substituent of the alkyl, alkoxy or alkylthio group for $R^6$; the substituent of the alkyl, alkoxy or alkylthio group for $R^7$; and the substituent of the alkyl for $R^{7a}$ include halogen atoms, cyano group, protected or unprotected carboxyl groups, protected or unprotected hydroxyl groups, protected or unprotected amino groups, protected or unprotected lower alkylamino groups, lower alkyl groups, lower alkoxy groups, lower alkoxycarbonyl groups, aryl groups, cycloalkyl groups, lower alkenyl groups and halogen atom-substituted lower alkyl groups, and the $R^2$, $R^3$, $R^4$, $R^5$, $R^6$, $R^7$ and $R^{7a}$ groups may be substituted by one or two or more of these groups.

Moreover, as the substituent of the alkyl for $R^{7a}$, a halogen atom is preferable.

The ring comprising the boron atom which $R^8$ and $R^9$ form when taken together includes 5-membered to 8-membered rings containing at least one hetero atom selected from oxygen atom and nitrogen atom as the hetero atom forming the ring and condensed rings thereof, for example, 1,3,2-dioxaborolane, 1,3,2-dioxaborinane, 1,3,5,2-dioxazaborinane, 1,3,5,2-trioxaborinane, 1,3,6,2-trioxaborocane, 1,3,6,2-dioxazaborocane and the like.

The leaving group for $X^2$ includes halogen atoms such as chlorine atom, bromine atom, iodine atom and the like; halogen-substituted or unsubstituted alkylsulfonyloxy groups such as methylsulfonyloxy, trifluoromethylsulfonyloxy and the like; and arylsulfonyloxy groups such as p-fluorophenylsulfonyloxy and the like.

As the alkyl group for $R^{4a}$, a lower alkyl group is preferable.

I. Process for Producing Compound of the General formula [1] and Process for Producing Compound of the General Formula [2a]

Production Process IA

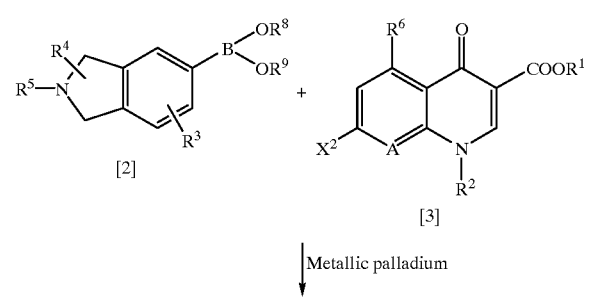

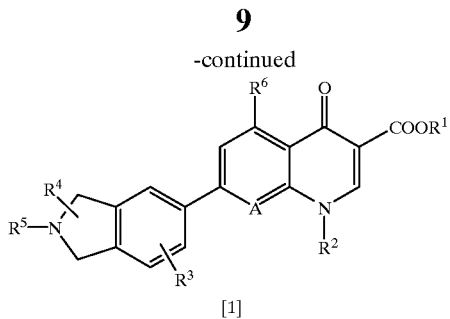

Production Process IB

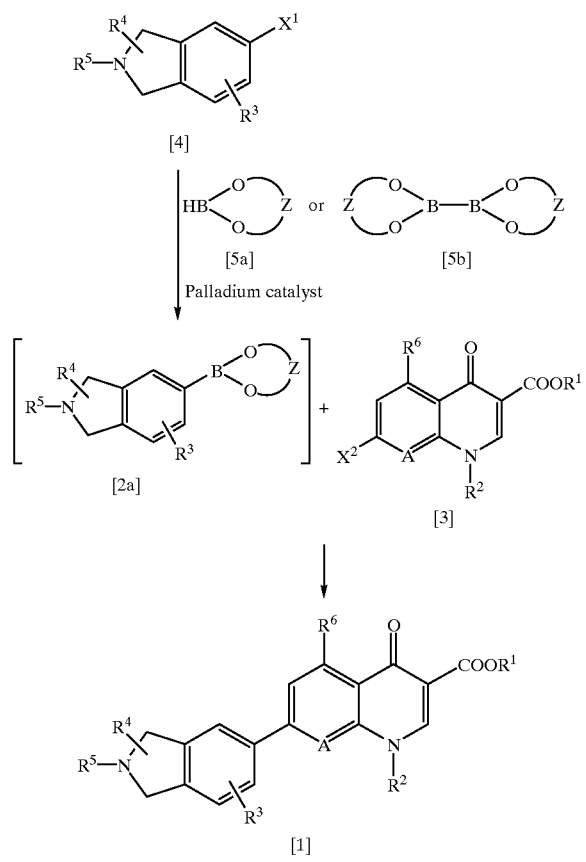

wherein $R^1, R^2, R^3, R^4, R^5, R^6, R^8, R^9, X^1, X^2$, A and Z have the same meanings as mentioned above.

The compounds of the general formulas [1], [2], [2a], [3], [4], [5a] and [5b] may be in the form of salts. As the salts, there can be mentioned usually known salts at basic groups such as amino group and the like and at acidic groups such as hydroxyl group, carboxyl group and the like. As the salts at basic groups, there can be mentioned, for example, salts with mineral acids such as hydrochloric acid, hydrobromic acid, sulfuric acid and the like; salts with organic carboxylic acids such as tartaric acid, formic acid, lactic acid, citric acid, trichloroacetic acid, trifluoroacetic acid and the like; and salts with sulfonic acids such as methanesulfonic acid, benzenesulfonic acid, p-toluenesulfonic acid, mesitylene-sulfonic acid, naphthalenesulfonic acid and the like. Moreover, the salts at acidic groups, there can be mentioned, for example, salts with alkali metals such as sodium, potassium and the like; salts with alkaline earth metals such as calcium, magnesium and the like; salts with ammonium; salts with nitrogen-containing organic bases such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-b-phenethylamine, 1-ephenamine, N,N'-dibenzylethylenediamine and the like; etc.

Production Process IA (1) Process for Producing Compound of the General Formula [1] or its Salt The compound of the general formula [1] or its salt can be produced by subjecting a compound of the general formula [2] or its salt and a compound of the general formula [3] or its salt to coupling reaction using metallic palladium in the presence or absence of a base.

The solvent which is used in this reaction is not particularly limited as far as it does not adversely affect the reaction, and includes, for example, water; alcohols such as methanol, ethanol, propanol and the like; aromatic hydrocarbons such as benzene, toluene, xylene and the like; halogenated hydrocarbons such as methylene chloride, chloroform, dichloroethane and the like; ethers such as dioxane, tetrahydrofuran, anisole, diethylene glycol diethyl ether, dimethyl Cellosolve and the like; esters such as ethyl acetate, butyl acetate and the like; ketones such as acetone, methyl ethyl ketone and the like; nitrites such as acetonitrile and the like; amides such as N,N-dimethylformamide, N,N-dimethylacetamide and the like; sulfoxides such as dimethyl sulfoxide and the like; etc. These solvents may be used in admixture.

The base which is used, if desired, in this reaction includes, for example, potassium acetate, sodium hydrogencarbonate, sodium carbonate, potassium carbonate, triethylamine and the like. The amount of the base used is at least equal to the molar amount of, preferably 1 to 3 moles per mole of, the compound of the general formula [3] or its salt.

The metallic palladium used in this reaction includes, for example, palladium-activated carbon, palladium black and the like. The amount of the metallic palladium used is at least 0.00001 mole, preferably 0.001 to 0.05 mole, per mole of the compound of the general formula [3] or its salt.

The amount of the compound of the general formula [2] or its salt used is at least equal to the molar amount of, preferably 1.0 to 1.5 moles per mole of, the compound of the general formula [3] or its salt.

This coupling reaction may be usually carried out in an atmosphere of an inert gas (for example, argon, nitrogen) at 50–170° C. for 1 minute to 24 hours.

Incidentally, the compound of the general formula [3] or its salt can be produced by, for example, the method described in WO097/29102.

Production Process IIA (2.1) Process for Producing Compound of the General Formula [2a] or its Salt The compound of the general formula [2a] or its salt can be produced by reacting a compound of the general formula [4] or its salt with a dialkoxyborane of the general formula [5a] or an alkoxydiborane of the general formula [5b] in the presence or absence of a base using a palladium catalyst selected from metallic palladium, palladium salts and palladium complexes.

The solvent which is used in this reaction may be any solvent as far as it does not adversely affect the reaction, and includes, for example, aromatic hydrocarbons such as benzene, toluene, xylene and the like; aliphatic hydrocarbons such as n-hexane, cyclohexane and the like; halogenated hydrocarbons such as methylene chloride, chloroform, dichloroethane and the like; ethers such as dioxane, tetrahydrofuran, anisole, diethylene glycol diethyl ether, dimethyl Cellosolve and the like; esters such as ethyl acetate, butyl acetate and the like; ketones such as acetone, methyl ethyl ketone and the like; nitrites such as acetonitrile and the like; amides such as N,N-dimethylformamide, N,N-dimethylacetamide and the like; sulfoxides such as dimethylsulfoxide and the like; etc. These solvents may be used in admixture.

The base which is used, if desired, in this reaction includes, for example, potassium acetate, potassium tert-butoxide, diisopropylethylamine, pyridine, 1,8-diazabicyclo[5.4.0]-7-undecene, tributylamine, triethylamine and the like. The amount of the base used is at least equal to the molar amount of, preferably 1 to 3 moles per mole of, the compound of the general formula [4] or its salt.

The metallic palladium used in this reaction includes, for example, metallic palladium such as palladium-activated carbon, palladium black and the like; the palladium salt includes, for example, inorganic palladium salts such as palladium chloride and the like and organic palladium salts such as palladium acetate and the like; and the palladium complex includes, for example, organic palladium complexes such as tetrakis(triphenyl-phosphine)palladium(0), bis(triphenylphosphine)-palladium(II) chloride, 1,1'-bis(diphenylphosphino)-ferrocenepalladium(II) chloride and the like. The amount of a palladium catalyst selected from metallic palladium, palladium salt and palladium complex used may be at least 0.00001 mole, preferably 0.001 to 0.05 mole, per mole of the compound of the general formula [4] or its salt.

The dialkoxyborane which is used in this reaction includes, for example, 4,4,5,5-tetramethyl-1,3,2-dioxaborolane, catecholborane and the like, and the alkoxydiborane includes, for example, 4,4,5,5-tetramethyl-1,3,2-dioxaborolan-2-yl-4',4',5',5'-tetramethyl-1',3',2'-dioxaborolane and the like.

The amount thereof used is at least equal to the molar amount of, preferably 1.0 to 1.5 moles per mole of, the compound of the general formula [4] or its salt.

This reaction may be carried out in an atmosphere of an inert gas (for example, argon, nitrogen) at 0–150° C., preferably 80–110° C., for 1–24 hours.

(2.2) Process for Producing Compound of the General Formula [1] or its Salt

The compound of the general formula [1] or its salt can be produced by adding the compound of the general formula [2a] or its salt produced in the above (2.1) without isolation to the reaction mixture and, if necessary, additionally adding a palladium catalyst, adding thereto the compound of the general formula [3] or its salt in the presence or absence of a base in an atmosphere of an inert gas (for example, argon, nitrogen), and further subjecting them to reaction.

When the compounds of the general formulas [2], [2a], [3] and [4] or their salts in the above-mentioned production process have isomers (for example, optical isomers, geometric isomers, tautomers and the like), these isomers can be used, and their solvates, hydrates and crystals of various forms can be used.

Furthermore, the amino groups of the compounds of the general formulas [2], [2a], [3] and [4] or their salts can be previously protected with a conventional protecting group and the protecting group can be removed in a manner known per se after the reaction.

The thus produced compound of the general formula [1] or its salt can be isolated and purified in at least one conventional manner such as extraction, crystallization, column chromatography or the like.

Among the compounds of the general formula [1] produced by the process of this invention, there can be mentioned, as preferable compounds, compounds of the general formula [1] wherein $R^2$ is a substituted or unsubstituted cycloalkyl group; $R^3$ is a hydrogen atom, a halogen atom or an alkyl group; $R^4$ is a hydrogen atom or an alkyl group; $R^5$ is a hydrogen atom or an alkyl group; and A is CH or C—$R^7$ in which $R^7$ is a halogen atom, a halogen-substituted or unsubstituted lower alkyl or lower alkoxy group. As representative compounds, there are mentioned, for example, the following compounds:

1-cyclopropyl-7-(isoindolin-5-yl)-1,4-dihydro-4-oxoquinoline-3-carboxylic acid, 8-chloro-1-cyclopropyl-7-(isoindolin-5-yl)-1,4-dihydro-4-oxoquinoline-3-carboxylic acid, 1-cyclopropyl-8-fluoro-7-(isoindolin-5-yl)-1,4-dihydro-4-oxoquinoline-3-carboxylic acid, 1-cyclopropyl-7-(isoindolin-5-yl)-8-methyl-1,4-dihydro-4-oxoquinoline-3-carboxylic acid, 1-cyclopropyl-7-(isoindolin-5-yl)-8-methoxy-1,4-dihydro-4-oxoquinoline-3-carboxylic acid, 1-cyclopropyl-8-difluoromethoxy-7-(isoindolin-5-yl)-1,4-dihydro-4-oxoquinoline-3-carboxylic acid, 1-cyclopropyl-7-(isoindolin-5-yl)-8-trifluoro-methyl-1,4-dihydro-4-oxoquinoline-3-carboxylic acid, 7-(7-chloroisoindolin-5-yl)-1-cyclopropyl-8-methyl-1,4-dihydro-4-oxoquinoline-3-carboxylic acid, 1-cyclopropyl-7-(7-fluoroisoindolin-5-yl)-1,4-dihydro-4-oxoquinoline-3-carboxylic acid, 1-cyclopropyl-7-(7-fluoroisoindolin-5-yl)-8-methyl-1,4-dihydro-4-oxoquinoline-3-carboxylic acid, 1-cyclopropyl-7-(7-fluoroisoindolin-5-yl)-8-methoxy-1,4-dihydro-4-oxoquinoline-3-carboxylic acid, 1-cyclopropyl-8-difluoromethoxy-7-(7-fluoroisoindolin-5-yl)-1,4-dihydro-4-oxoquinoline-3-carboxylic acid, 1-cyclopropyl-7-(7-fluoroisoindolin-5-yl)-8-trifluoromethyl-1,4-dihydro-4-oxoquinoline-3-carboxylic acid, 1-cyclopropyl-8-methoxy-7-(7-methylisoindolin-5-yl)-1,4-dihydro-4-oxoquinoline-3-carboxylic acid, 1-cyclopropyl-7-(2-methylisoindolin-5-yl)-1,4-dihydro-4-oxoquinoline-3-carboxylic acid, 1-cyclopropyl-8-methyl-7-(2-methylisoindolin-5-yl)-1,4-dihydro-4-oxoquinoline-3-carboxylic acid, 1-cyclopropyl-8-methoxy-7-(2-methylisoindolin-5-yl)-1,4-dihydro-4-oxoquinoline-3-carboxylic acid, 1-cyclopropyl-8-difluoromethoxy-7-(2-methyl-isoindolin-5-yl)-1,4-dihydro-4-oxoquinoline-3-carboxylic acid, 1-cyclopropyl-7-(2-methylisoindolin-5-yl)-8-trifluoromethyl-1,4-dihydro-4-oxoquinoline-3-carboxylic acid, (±)-1-cyclopropyl-7-(1-methylisoindolin-5-yl)-1,4-dihydro-4-oxoquinoline-3-carboxylic acid, (±)-1-cyclopropyl-8-methyl-7-(1-methylisoindolin-5-yl)-1,4-dihydro-4-oxoquinoline-3-carboxylic acid, (+)-1-cyclopropyl-8-methyl-7-(1-methylisoindolin-5-yl)-1,4-dihydro-4-oxoquinoline-3-carboxylic acid, (−)-1-cyclopropyl-8-methyl-7-(1-methylisoindolin-5-yl)-1,4-dihydro-4-oxoquinoline-3-carboxylic acid, (±)-1-cyclopropyl-8-methoxy-7-(1-methyl-isoindolin-5-yl)-1,4-dihydro-4-oxoquinoline-3-carboxylic acid, (+)-1-cyclopropyl-8-methoxy-7-(1-methyl-isoindolin-5-yl)-1,4-dihydro-4-oxoquinoline-3-carboxylic acid, (−)-1-cyclopropyl-8-methoxy-7-(1-methyl-isoindolin-5-yl)-1,4-dihydro-4-oxoquinoline-3-carboxylic acid, (±)-1-cyclopropyl-8-difluoromethoxy-7-(1-methyl-isoindolin- 5-yl)-1,4-dihydro-4-oxoquinoline-3-carboxylic acid, (+)-1-cyclopropyl-8-difluoromethoxy-7-(1-methylisoindolin-5-yl)-1,4-dihydro-4-oxoquinoline-3-carboxylic acid,
(−)-1-cyclopropyl-8-difluoromethoxy-7-(1-methylisoindolin-5-yl)-1,4-dihydro-4-oxoquinoline-3-carboxylic acid,
1-cyclopropyl-7-(4-fluoroisoindolin-5-yl)-1,4-dihydro-4-oxoquinoline-3-carboxylic acid,
1-cyclopropyl-7-(4-fluoroisoindolin-5-yl)-8-methyl-1,4-dihydro-4-oxoquinoline-3-carboxylic acid,
1-cyclopropyl-7-(4-fluoroisoindolin-5-yl)-8-methoxy-1,4-dihydro-4-oxoquinoline-3-carboxylic acid,
1-cyclopropyl-8-difluoromethoxy-7-(4-fluoro-isoindolin-5-yl)-1,4-dihydro-4-oxoquinoline-3-carboxylic acid,
1-cyclopropyl-7-(4-fluoroisoindolin-5-yl)-8-trifluoromethyl-1,4-dihydro-4-oxoquinoline-3-carboxylic acid,
1-cyclopropyl-7-(6-fluoroisoindolin-5-yl)-1,4-dihydro-4-oxoquinoline-3-carboxylic acid,
1-cyclopropyl-7-(6-fluoroisoindolin-5-yl)-8-methyl-1,4-dihydro-4-oxoquinoline-3-carboxylic acid,
1-cyclopropyl-7-(6-fluoroisoindolin-5-yl)-8-methoxy-1,4-dihydro-4-oxoquinoline-3-carboxylic acid,
1-cyclopropyl-8-difluoromethoxy-7-(6-fluoro-isoindolin-5-yl)-1,4-dihydro-4-oxoquinoline-3-carboxylic acid,
1-cyclopropyl-7-(6-fluoroisoindolin-5-yl)-8-trifluoromethyl-1,4-dihydro-4-oxoquinoline-3-carboxylic acid,
1-cyclopropyl-7-(4,7-difluoroisoindolin-5-yl)-1,4-dihydro-4-oxoquinoline-3-carboxylic acid,
1-cyclopropyl-7-(4,7-difluoroisoindolin-5-yl)-8-methyl-1,4-dihydro-4-oxoquinoline-3-carboxylic acid,
1-cyclopropyl-7-(4,7-difluoroisoindolin-5-yl)-8-methoxy-1,4-dihydro-4-oxoquinoline-3-carboxylic acid,
1-cyclopropyl-7-(4,7-difluoroisoindolin-5-yl)-8-difluoromethoxy-1,4-dihydro-4-oxoquinoline-3-carboxylic acid, and
1-cyclopropyl-7-(4,7-difluoroisoindolin-5-yl)-8-difluoromethoxy-1,4-dihydro-4-oxoquinoline-3-carboxylic acid.

Furthermore, among the compounds of the general formula [2a] produced by the process of this invention, there can be mentioned, as preferable compounds, compounds of the general formula [2a] wherein $R^3$ is a hydrogen atom, a halogen atom or an alkyl group; $R^4$ is a hydrogen atom or an alkyl group; $R^5$ is a hydrogen atom or an alkyl group; and Z is 1,1,2,2-tetramethylethylene, and as representative compounds, there are mentioned, for example, the following compounds:

5-(4,4,5,5-tetramethyl-1,3,2-dioxaborolan-2-yl)isoindoline,
7-chloro-5-(4,4,5,5-tetramethyl-1,3,2-dioxaborolan-2-yl)isoindoline,
7-fluoro-5-(4,4,5,5-tetramethyl-1,3,2-dioxaborolan-2-yl)isoindoline,
7-methyl-5-(4,4,5, 5-tetramethyl-1,3,2-dioxaborolan-2-yl)isoindoline,
2-methyl-5-(4,4,5,5-tetramethyl-1,3,2-dioxaborolan-2-yl)isoindoline,
1-methyl-5-(4,4,5,5-tetramethyl-1,3,2-dioxaborolan-2-yl)isoindoline,
(±)-1-methyl-5-(4,4,5,5-tetramethyl-1,3,2-dioxaborolan-2-yl)isoindoline,
(+)-1-methyl-5-(4,4,5,5-tetramethyl-1,3,2-dioxaborolan-2-yl)isoindoline,
(−)-1-methyl-5-(4,4,5,5-tetramethyl-1,3,2-dioxaborolan-2-yl)isoindoline,
4-fluoro-5-(4,4,5,5-tetramethyl-1,3,2-dioxaborolan-2-yl)isoindoline,
6-fluoro-5-(4,4,5,5-tetramethyl-1,3,2-dioxaborolan-2-yl)isoindoline, and
4,7-difluoro-5-(4,4,5,5-tetramethyl-1,3,2-dioxaborolan-2-yl)isoindoline.

II. Process for Producing 1-alkylisoindoline-5-boronic Acid Derivative

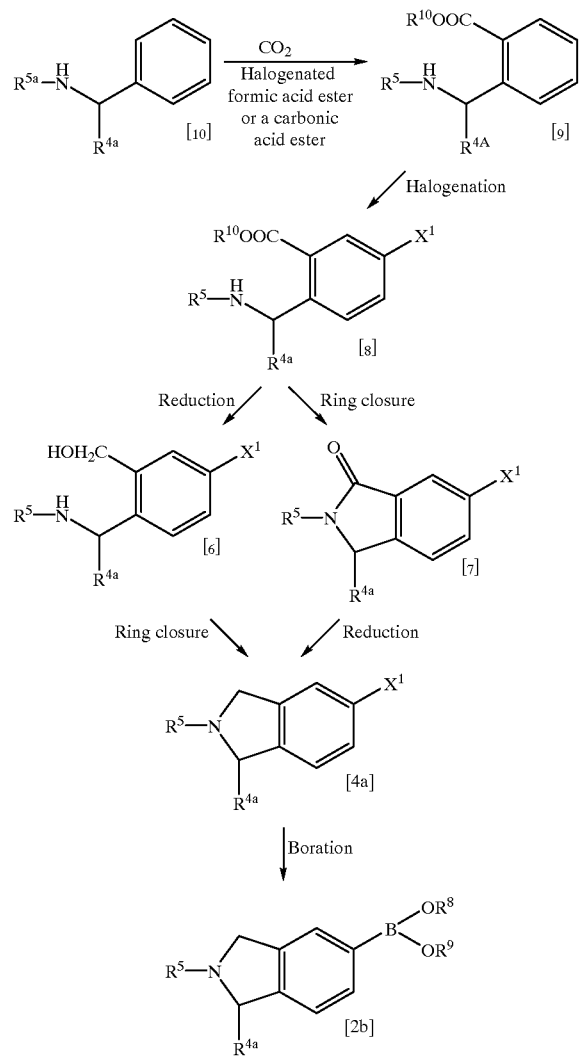

wherein $R^{4a}$, $R^5$, $R^8$, $R^9$ and $X^1$ have the same meanings as mentioned above, $R^5a$ represents a substituted or unsubstituted alkyl, cycloalkyl, alkylsulfonyl, arylsulfonyl, acyl or aryl group, and $R^{10}$ represents a hydrogen atom or a carboxyl-protecting group.

The compounds of the general formulas [2b], [4a], [6], [7], [8], [9] and [10] can also be used in the form of salts, and as the salts, there can be mentioned usually known salts at basic groups such as amino group and the like and at acidic groups such as hydroxyl group, carboxyl group and the like. The salt at basic group includes, for example, salts with mineral acids such as hydrochloric acid, hydrobromic acid, sulfuric acid and the like; salts with organic carboxylic acids such as tartaric acid, formic acid, lactic acid, citric acid, trichloroacetic acid, trifluoroacetic acid and the like; and salts with sulfonic acids such as methanesulfonic acid, benzenesulfonic acid, p-toluenesulfonic acid, mesitylenesulfonic acid, naphthalenesulfonic acid and the like. Furthermore, the salt at acidic group includes, for example, salts with alkali metals such as sodium, potassium and the like; salts with alkaline earth metals such as calcium, magnesium and the like; salts with ammonium; salts with nitrogen-containing organic bases such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-b-phenethylamine, 1-ephenamine, N,N'-dibenzylethylenediamine and the like; etc.

(1) Process for Producing Compound of the General Formula [9] or its Salt

The compound of the general formula [9] or its salt can be produced by reacting a compound of the general formula [10] or its salt with carbon dioxide, a halogenated formic acid ester or a carbonic acid ester in the presence of a base.

The solvent which is used in this reaction may be any solvent as far as it does not adversely affect the reaction, and includes, for example, aliphatic hydrocarbons such as n-hexane, cyclohexane and the like; ethers such as diethyl ether, 1,2-dimethoxyethane, tetrahydrofuran, dioxane and the like; etc. These solvents may be used in admixture.

The base which is used in this reaction includes, for example, alkyl metal or aryl metal reagents such as n-butyllithium, tert-butyllithium, phenyllithium, methyllithium and the like; and amide bases such as lithium diisopropylamide, lithium bistrimethylsilylamide and the like.

The halogenated formic acid ester includes, for example, methyl chloroformate, ethyl chloroformate and the like.

The carbonic acid ester includes, for example, dimethyl carbonate, diethyl carbonate, diphenyl carbonate and the like.

The amounts of the base and carbon dioxide, halogenated formic acid ester or carbonic acid ester used are at least 2 moles, preferably 2 to 3 moles, per mole of the compound of the general formula [10] or its salt.

This reaction may be usually carried out at −70 to 20° C., preferably −50 to 0° C., for 10 minutes to 24 hours.

The obtained compound of the general formula [9] or its salt may be used as it is without isolation in the subsequent reaction.

(2) Process for Producing Compound of the General Formula [8] or its Salt

The compound of the general formula [8] or its salt can be produced by subjecting the compound of the general formula [9] or its salt to halogenation reaction.

The solvent which is used in this reaction may be any solvent as far as it does not adversely affect the reaction, and includes, for example, carboxylic acids such as acetic acid and the like; halogenated hydrocarbons such as carbon tetrachloride and the like; inorganic acids such as sulfuric acid, hydrochloric acid and the like; water; etc. These solvents may be used in admixture.

The halogenating agent which is used in this reaction includes, for example, halogens such as chlorine, bromine, iodine and the like; organic halogen compounds such as N-bromosuccinimide, halogenated isocyanuric acids such as sodium N-bromoisocyanurate and the like; etc.

The amount of the halogenating agent used is at least equal to the molar amount of, preferably 1 to 1.5 moles per mole of, the compound of the general formula [9] or its salt.

This reaction may be carried out at −10 to 100° C., preferably 0 to 30° C., for 10 minutes to 24 hours.

The obtained compound of the general formula [8] or its salt may be used as it is without isolation in the subsequent reaction.

(3) Process for Producing Compound of the General Formula [4a] or its Salt The compound of the general formula [4a] or its salt can be produced by reducing the compound of the general formula [8] or its salt to produce a compound of the general formula [6] or its salt and thereafter subjecting the compound of the general formula [6] or its salt to ring-closing reaction or alternatively by ring-closing the compound [8] or its salt to produce a compound of the general formula [7] or its salt and thereafter subjecting the compound of the general formula [7] or its salt to reduction reaction.

The solvent which is used in this reduction reaction may be any solvent as far as it does not adversely affect the reaction, and includes, for example, alcohols such as methanol, ethanol, isopropanol and the like; ethers such as tetrahydrofuran, dioxane, 1,2-dimethoxyethane, diethylene glycol dimethyl ether and the like; nitriles such as acetonitrile and the like; amides such as N,N-dimethylformamide and the like; sulfoxides such as dimethylsulfoxide and the like; water; etc. These solvents may be used in admixture.

The reducing agent which is used in this reaction includes, for example, alkali metals such as lithium, sodium, potassium and the like; alkaline earth metals such as magnesium, calcium and the like; metals and their salts such as zinc, aluminum, chromium, titanium, iron, samarium, selenium, sodium hydrosulfite and the like; metal hydrides such as diisobutylaluminum hydride, trialkylaluminum hydride, tin hydride compound, hydrosilane and the like; borohydride complex compounds such as sodium borohydride, lithium borohydride, potassium borohydride, calcium borohydride and the like; aluminum hydride complex compounds such as lithium aluminum hydride and the like, etc.; boranes; alkylboranes; and the like.

The amount of the reducing agent used in this reaction is varied depending upon the kind of the reducing agent; however, at least 0.25 mole is required and, for example, in the case of the boron hydride complex compound, the above amount is at least 0.25 mole, preferably 0.25 to 2 moles, per mole of the compound of the general formula [8] or [7] or its salt.

This reaction may be carried out usually at −20 to 100° C., preferably 0 to 50° C., for 10 minutes to 24 hours.

The solvent which is used in this ring-closing reaction may be any solvent as far as it does not adversely affect the reaction, and includes, for example, ethers such as tetrahydrofuran, dioxane, 1,2-dimethoxyethane, diethylene glycol dimethyl ether and the like; nitrites such as acetonitrile and the like, amides such as N,N-dimethylformamide and the like; sulfoxides such as dimethylsulfoxide and the like; aromatic hydrocarbons such as benzene, toluene, xylene and the like; water; etc. These solvents may be used in admixture.

When the compound of the general formula [8] or its salt is subjected to ring-closing reaction to produce a compound of the general formula [7] or its salt, or when the compound of the general formula [6] or its salt is subjected to activation of its hydroxyl group and thereafter to ring-closing reaction to produce a compound of the general formula [4a] or its salt, the base which is if desired used includes, for example, sodium hydroxide, potassium hydroxide, sodium tert-butoxide, potassium tert-butoxide, sodium hydride and the like, and the amount of the base used is at least equal to the molar amount of, preferably 1 to 1.5 moles per mole of, the compound of the general formula [8] or [6] or its salt.

Furthermore, as the catalyst which is if desired used, a usually known phase transfer catalyst of quaternary ammonium salt is used; however, preferable are tetra-n-butylammonium bromide, tetra-n-butylammonium hydrogen-sulfate and the like. The amount of the catalyst used is 0.01 to 0.2 mole per mole of the compound of the formula [8] or [6] or its salt.

This reaction may be carried out at usually 0 to 100° C., preferably 0 to 30° C., for 10 minutes to 24 hours.

The obtained compound of the general formula [4a] or its salt may be used as it is without isolation in the subsequent reaction.

(4) Process for Producing Compound of the General Formula [2b] or its Salt

The compound of the general formula [2b] or its salt can be produced by subjecting the compound of the general formula [4a] or its salt to borodation.

Specifically, according to, for example, the method described in Jikken Kagaku Koza, 4th edition, Vol. 24, pages 61–90 (1992), it can be obtained by subjecting a compound of the formula [4b] or its salt to lithiation or Grignard reaction and thereafter to reaction with a trialkyl borate.

The solvent which is used in this reaction may be any solvent as far as it does not adversely affect the reaction, and includes, for example, aliphatic hydrocarbons such as n-hexane, cyclohexane and the like; ethers such as diethyl ether, 1,2-dimethoxyethane, tetrahydrofuran, dioxane and the like; etc. These solvents may be used in admixture.

The lithiating agent which is used in this reaction includes, for example, alkyl metal reagents such as n-butyllithium, tert-butyllithium, phenyllithium, methyl-lithium and the like; and amide bases such as lithium diisopropylamide, lithium bistrimethylsilylamide and the like. Moreover, the Grignard reagent can be obtained by reacting metallic magnesium with the compound represented by the general formula [4a] or its salt.

The trialkyl borate which is used in this reaction includes, for example, trimethyl borate, triethyl borate, triisopropyl borate, tributyl borate and the like.

The amount of the lithionizing agent, metallic magnesium or trialkyl borate used is at least equal to the molar amount of, preferably 1 to 2 moles per mole of, the compound of the general formula [4a] or its salt.

This reaction may be carried out usually at −70 to 50° C., preferably −60 to 0° C., for 10 minutes to 24 hours.

The obtained compound of the general formula [2b] or its salt may be used as it is without isolation in the subsequent reaction.

The thus obtained compound of the general formula [2b] or its salt can be subjected to, for example, protection or deprotection to be converted to the other compound of the general formula [2b] or its salt.

When the compounds of the general formula [2b], [4a], [6], [7], [8], [9] and [10] or their salts in the above-mentioned production process have isomers (for example, optical isomers, geometrical isomers, tautomers and the like), these isomers can be used, and their solvates, hydrates and crystals of various forms can also be used.

When the compounds of the general formulas [4a], [6], [7], [8], [9] and [10] or their salts have an amino group, a hydroxyl group or a carboxyl group, it is also possible to previously protect these groups with a conventional protecting group and remove the protecting group after the reaction in a manner known per se.

Next, the process for producing a compound of the general formula [1a] or its salt using the compound of the general formula [2b] or its salt as the starting material is explained.

Production Process IIB

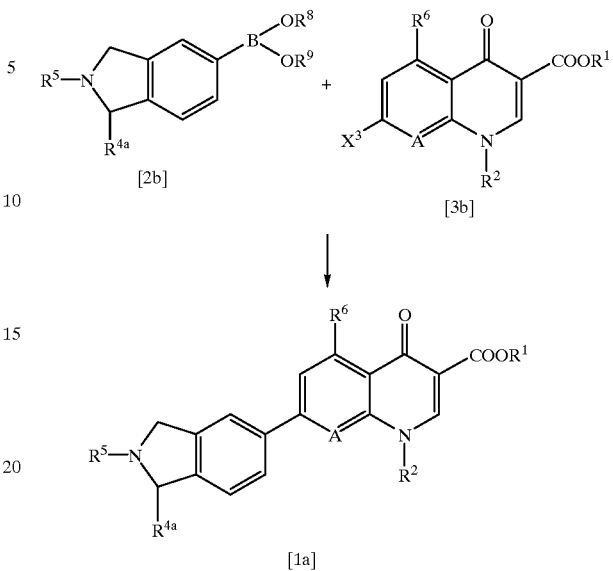

wherein $R^1$, $R^2$, $R^{4a}$, $R^5$, $R^6$, $R^8$, $R^9$, $X^3$ and A have the same meanings as mentioned above.

The compound of the general formula [1a] or its salt can be obtained by subjecting a compound of the general formula [3b] or its salt and the compound of the general formula [2b] or its salt to coupling reaction using a palladium complex catalyst in the presence or absence of a base.

The solvent which is used in this reaction may be any solvent as far as it does not adversely affect the reaction, and includes, for example, water; alcohols such as methanol, ethanol, propanol and the like; aromatic hydrocarbons such as benzene, toluene, xylene and the like; halogenated hydrocarbons such as methylene chloride, chloroform, dichloroethane and the like; ethers such as dioxane, tetrahydrofuran, anisole, diethylene glycol diethyl ether, dimethyl Cellosolve and the like; esters such as ethyl acetate, butyl acetate and the like; ketones such as acetone, methyl ethyl ketone and the like; nitrites such as acetonitrile and the like; amides such as N,N-dimethylformamide, N,N-dimethylacetamide and the like; sulfoxides such as dimethylsulfoxide and the like; etc. These solvents may be used in admixture.

The base which is used, if desired, in this reaction includes, for example, sodium hydrogencarbonate, sodium carbonate, potassium carbonate, triethylamine and the like.

The palladium complex catalyst which is used in this reaction includes, for example, inorganic palladium salts such as palladium chloride and the like; organic palladium salts such as palladium acetate and the like; and organic palladium complexes such as tetrakis(triphenyl-phosphine)palladium(0), bis(triphenylphosphine)-palladium(II) chloride, 1,1'-bis(diphenylphosphino)-ferrocenepalladium(II) chloride and the like.

The amount of the compound of the general formula [2b] or its salt used is at least equal to the molar amount of, preferably 1.0 to 1.5 moles per mole of, the compound of the general formula [3b] or its salt.

This coupling reaction may be carried out usually in an atmosphere of an inert gas (for example, argon, nitrogen) at 50 to 170° C. for 1 minute to 24 hours.

The salt of the compound of the general formula [1a] includes, for example, the same salts as those mentioned as to the compounds of the general formulas [2b], [4a], [6], [7], [8], [9] and [10].

The compound of the general formula [3b] or its salt can be produced by, for example, the method described in WO097/29102.
III. Process for producing 1-alkyl-5-halogenoiso-indoline derivative
Production Process IIIA

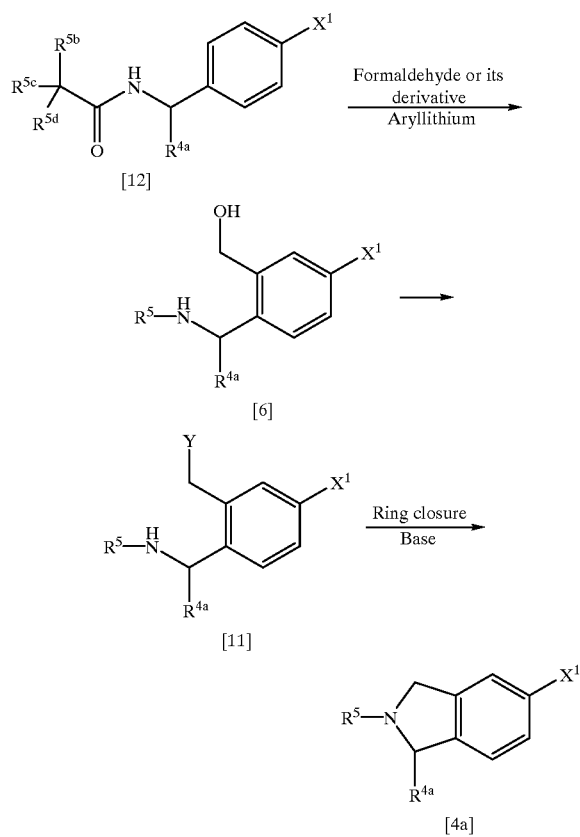

wherein $R^{4a}$, $R^5$ and $X^1$ have the same meanings as mentioned above; $R^{5b}$, $R^{5c}$ and $R^{5d}$ may be the same or different and each represents an alkyl group; and Y represents a leaving group.

The leaving group for Y includes, for example, halogen atoms; lower alkylsulfonyloxy groups such as methylsulfonyloxy, ethylsulfonyloxy, isopropylsulfonyloxy and the like; arylsulfonyloxy groups such as phenylsulfonyloxy, naphthylsulfonyloxy and the like; etc.

Furthermore, as the alkyl groups for $R^{5b}$, $R^{5c}$ and $R^{5d}$, lower alkyl groups such as methyl group and the like are preferable.

The compounds of the general formulas [12] and [11] can also be converted to their salts, and as the salts, there can be mentioned usually known salts at basic groups such as amino group and the like. As the salts at the basic groups, there can be mentioned, for example, salts with mineral acids such as hydrochloric acid, hydrobromic acid, sulfuric acid and the like; salts with organic carboxylic acids such as tartaric acid, formic acid, lactic acid, citric acid, trichloroacetic acid, trifluoroacetic acid and the like; salts with sulfonic acids such as methanesulfonic acid, benzenesulfonic acid, p-toluenesulfonic acid, mesitylenesulfonic acid, naphthalenesulfonic acid and the like; etc.

Furthermore, the salts of the compounds of the general formulas [6] and [4a] in the present production process include the same salts as mentioned as to Production Process IIA.

(1) Process for Producing Compound of the General Formula [6] or its Salt

The compound of the general formula [6] or its salt can be produced by reacting the compound of the general formula [12] or its salt with a formaldehyde or its derivative in the presence of an aryllithium.

The solvent which is used in this reaction may be any solvent as far as it does not adversely affect the reaction, and includes, for example, aliphatic hydrocarbons such as n-hexane, cyclohexane and the like; ethers such as diethyl ether, n-dibutyl ether, 1,2-dimethoxyethane, tetrahydrofuran, dioxane and the like. These solvents may be used in admixture.

The aryllithium which is used in this invention includes, for example, phenyllithium, biphenyllithium, naphthyllithium and the like.

The formaldehyde or its derivative includes, for example, formaldehyde, paraformaldehyde, trioxane and the like.

The amounts of the aryllithium and the formaldehyde or its derivative used are at least 2 moles, preferably 2 to 5 moles, per mole of the compound of the general formula [12] or its salt.

This reaction may be carried out at usually −70 to 50° C., preferably −30 to 30° C., for 10 minutes to 24 hours.

The obtained compound of the general formula [6] or its salt may be used as it is without isolation in the subsequent reaction.

Moreover, the amino-protecting group may be subjected to elimination reaction after the reaction and a new amino-protecting group may be introduced.

(2) Process for Producing Compound of the General Formula [11] or its Salt

The compound of the general formula [11] or its salt can be produced by reacting the compound of the general formula [6] or its salt with a halogenating agent, a sulfonylating agent or the like in the presence or absence of a base.

The solvent which is used in this reaction may be any solvent as far as it does not adversely affect the reaction, and includes, for example, aliphatic hydrocarbons such as n-hexane, cyclohexane and the like; halogenated hydrocarbons such as methylene chloride, chloroform and the like; ethers such as tetrahydrofuran, 1,2-dimethoxyethane, dioxane and the like; aromatic hydrocarbons such as benzene, toluene, xylene and the like; sulfoxides such as dimethylsulfoxide and the like; amides such as N,N-dimethylformamide and the like; esters such as ethyl acetate and the like; nitrites such as acetonitrile and the like; etc. These solvents may be used in admixture.

Moreover, the base which is used, if necessary, includes, for example, organic and inorganic bases such as triethylamine, diisopropylethylamine, 1,8-diazabicyclo-[5.4.0]undec-7-ene (DBU), pyridine, potassium tert-butoxide, sodium carbonate, potassium carbonate, sodium hydride and the like.

The halogenating agent includes, for example, phosphorus oxychloride, phosphorous oxybromide, phosphorus trichloride, phosphorus pentachloride, thionyl chloride and the like.

The sulfonylating agent includes, for example, methanesulfonyl chloride, p-toluenesulfonyl chloride and the like.

The amount of the halogenating agent or sulfonylating agent used and the amount of the base which is used, if necessary, are at least equal to the molar amount of, preferably 1 to 5 moles per mole of, the compound of the general formula [6] or its salt.

This reaction may be carried out at usually −10 to 100° C., preferably 0 to 50° C., for 10 minutes to 24 hours.

The salt of the obtained compound of the general formula [11] or its salt may be used as it is without isolation in the subsequent reaction.

(3) Process for Producing Compound of the General Formula [4a] or its Salt

The compound of the general formula [4a] or its salt can be produced by subjecting the compound of the general formula [11] or its salt to ring-closing reaction in the presence of a base and in the presence or absence of a catalyst.

The solvent which is used in this reaction may be any solvent as far as it does not adversely affect the reaction, and includes, for example, aliphatic hydrocarbons such as n-hexane, cyclohexane and the like; aromatic hydrocarbons such as benzene, toluene and the like; ethers such as tetrahydrofuran, dioxane, diethylene glycol dimethyl ether, di-n-butyl ether and the like; halogenated hydrocarbons such as methylene chloride, chloroform and the like; nitrites such as acetonitrile and the like; amides such as N,N-dimethylformamide and the like; sulfoxides such as dimethylsulfoxide and the like; water; etc. These solvents may be used in admixture.

The base which is used in this reaction includes, for example, sodium hydroxide, potassium hydroxide, potassium tert-butoxide, sodium hydride and the like.

As the catalyst which is used, if necessary, there are used phase transfer catalysts of usually known quaternary ammonium salts. However, preferably, there are mentioned tetra-n-butylammonium bromide, tetra-n-butyl-ammonium hydrogensulfate and the like.

The amount of the base used is at least equal to the molar amount of, preferably 1 to 10 moles per mole of, the compound of the general formula [11] or its salt, and the amount of the catalyst which is used, if necessary, is 0.01 to 0.2 mole per mole of the compound of the general formula [11] or its salt.

This reaction may be carried out at usually 0 to 100° C., preferably 0 to 40° C., for 10 minutes to 24 hours.

The compound of the general formula [4a] or its salt may be used as it is without isolation in the subsequent reaction.

Furthermore, if necessary, after the removal of the protecting group of $R^5$, a new protecting group may be introduced into the compound of the general formula [4a] or its salt taking the subsequent production route into consideration.

When the compounds of the general formulas [4a], [6], [11] and [12] or their salts in the above-mentioned production process have isomers (for example, optical isomers, geometrical isomers, tautomers and the like), these isomers can be used. Also, solvates, hydrates and crystals of various forms can be used.

Moreover, when the compounds of the general formulas [4a], [6], [11] and [12] or their salts have an amino group, a hydroxyl group or a carboxyl group, it is possible to previously protect these groups with a conventional protecting group and remove the protecting group after the reaction in a manner known per se.

Next, a process for producing a compound of the general formula [1a] or its salt using the compound of the general formula [4a] or its salt as the starting material is explained.

Production Process IIIB

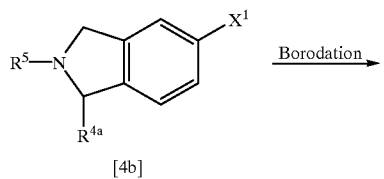

[4b]

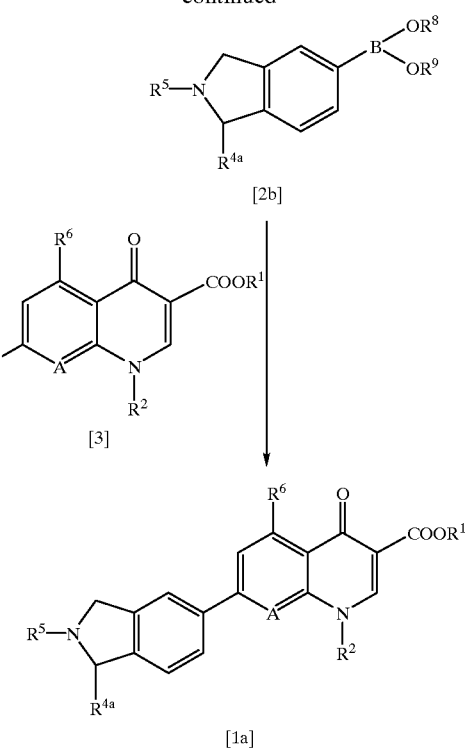

wherein $R^1$, $R^2$, $R^{4a}$, $R^5$, $R^6$, $R^8$, $R^9$, A, $X^1$ and $X^2$ have the same meanings as mentioned above.

(1) Process for Producing Compound of the General Formula [2b] or its Salt

The compound of the general formula [2b] or its salt can be produced by subjecting the compound of the general formula [4a] or its salt to borodation.

Specifically, it can be obtained by subjecting the compound of the general formula [4a] or its salt to lithiation or Grignard reaction according to, for example, the method described in Jikken Kagaku Koza, 4th edition, Vol. 24, pages 61–90 (1992), and thereafter to reaction with trialkyl borate.

The solvent which is used in this reaction may be any solvent as far as it does not adversely affect the reaction, and includes, for example, aliphatic hydrocarbons such as n-hexane, cyclohexane and the like; ethers such as diethyl ether, 1,2-dimethoxyethane, tetrahydrofuran, dioxane and the like; etc. These solvents may be used in admixture.

The lithiating agent which is used in this reaction includes, for example, alkyl metal or aryl metal reagents such as n-butyllithium, tert-butyllithium, phenyllithium, methyllithium and the like; and amide bases such as lithium diisopropylamide, lithium bistrimethylsilylamide and the like. Moreover, the Grignard reagent can be obtained by reacting metallic magnesium with the compound represented by the formula [4a] or its salt.

The trialkyl borate which is used in this reaction includes, for example, trimethyl borate, triethyl borate, triisopropyl borate, tributyl borate and the like.

The amounts of the lithiating agent, metallic magnesium and trialkyl borate used are at least equal to the molar amount of, preferably 1 to 2 moles per mole of, the compound of the general formula [4a] or its salt.

This reaction may be carried out at usually −70 to 50° C., preferably −60 to 0° C., for 10 minutes to 24 hours.

The obtained compound of the general formula [2b] or its salt may be used as it is without isolation in the subsequent reaction.

(2) Process for Producing Compound of the General Formula [1a] or its Salt

The compound of the general formula [1a] or its salt can be obtained by subjecting the compound of the general formula [2b] or its salt and the compound of the general formula [3] or its salt to coupling reaction using a palladium catalyst in the presence or absence of a base.

The solvent which is used in this reaction is not particularly limited as far as it does not adversely affect the reaction, and includes, for example, water; alcohols such as methanol, ethanol, propanol and the like; aromatic hydrocarbons such as benzene, toluene, xylene and the like; halogenated hydrocarbons such as methylene chloride, chloroform, dichloroethane and the like; ethers such as dioxane, tetrahydrofuran, anisole, diethylene glycol dimethyl ether, diethylene glycol diethyl ether, ethylene glycol dimethyl ether and the like; esters such as ethyl acetate, butyl acetate and the like; ketones such as acetone, methyl ethyl ketone and the like; nitriles such as acetonitrile and the like; amides such as N,N-dimethyl-formamide, N,N-dimethylacetamide and the like; sulfoxides such as dimethylsulfoxide and the like; etc. These solvents may be used in admixture.

The base which is used, if desired, in this reaction includes, for example, sodium hydrogencarbonate, sodium carbonate, potassium carbonate, triethylamine and the like, and the amount of the base used is at least equal to the molar amount of, preferably 2 to 5 moles per mole of, the compound of the general formula [3] or its salt.

Moreover, the palladium catalyst which is used in this reaction includes, for example, metallic palladium such as palladium-activated carbon, palladium black and the like; inorganic palladium salts such as palladium chloride and the like; organic palladium salts such as palladium acetate and the like; and organic palladium complexes such as tetrakis(triphenylphosphine)palladium(0), bis(triphenyl-phosphine)palladium(II) chloride, 1,1'-bis(diphenyl-phosphino)ferrocenepalladium(II) chloride and the like.

The amount of the palladium catalyst used is at least 0.00001 mole, preferably 0.001 to 0.05 mole, per mole of the compound of the general formula [3] or its salt.

The amount of the compound of the general formula [2b] or its salt used is at least equal to the molar amount of, preferably 1.0 to 1.5 moles per mole of, the compound of the general formula [3] or its salt.

This coupling reaction may be carried out usually in an atmosphere of an inert gas (for example, argon, nitrogen) at 50 to 170° C. for 1 minute to 24 hours.

The salts of the compounds of the general formulas [1a], [2b] and [3] in Production Process IIIB include the same salts as explained above.

The compound of the general formula [3] or its salt can be produced by, for example, the method described in WO097/29102.

IV. Process for Producing 7-bromoquinolonecarboxylic Acid Derivative

Production Process IVA

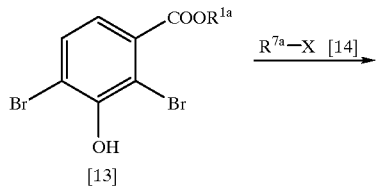

[13]

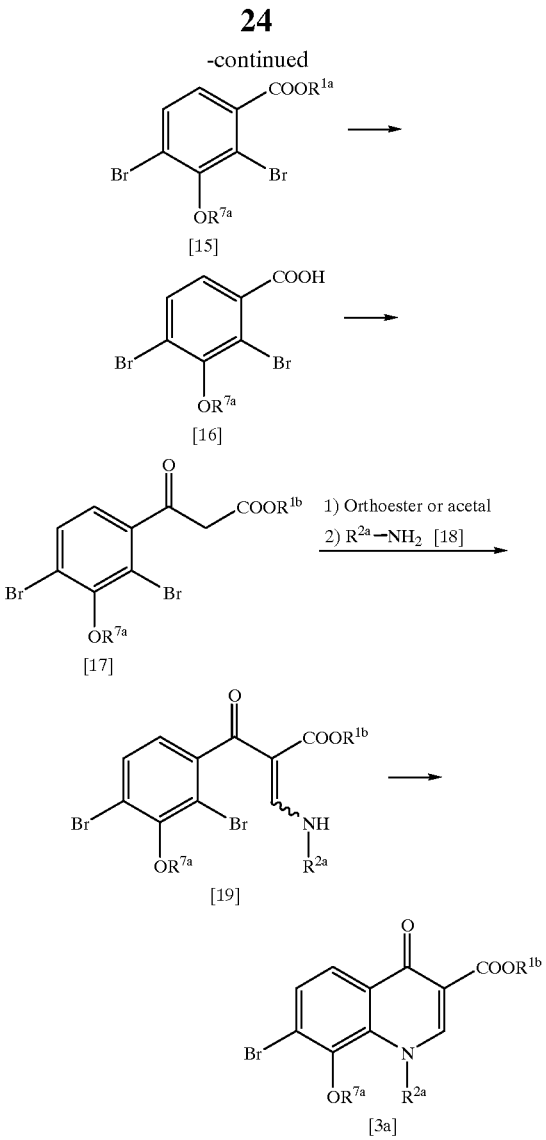

wherein $R^1$, $R^{2a}$ and $R^{7a}$ have the same meanings as mentioned above; $R^{1a}$ represents a carboxyl-protecting group; and X represents a halogen atom.

As the compounds of the general formulas [3a] and [13] to [19] can be converted to their salts, and as these salts, there can be mentioned usually known salts at basic groups such as amino group and the like and at acidic groups such as hydroxyl group, carboxyl group and the like. The salts at the basic groups include, for example, salts with mineral acids such as hydrochloric acid, hydrobromic acid, sulfuric acid and the like; salts with organic carboxylic acids such as tartaric acid, formic acid, lactic acid, citric acid, trichloroacetic acid, trifluoroacetic acid and the like; and salts with sulfonic acids such as methanesulfonic acid, benzenesulfonic acid, p-toluene-sulfonic acid, mesitylenesulfonic acid, naphthalenesulfonic acid and the like. Also, the salts at the acidic groups include, for example, salts with alkali metals such as sodium, potassium and the like; salts with alkaline earth metals such as calcium, magnesium and the like; salts with ammonium; salts with nitrogen-containing organic bases such as trimethylamine, triethylamine, tributylamine, pyridine, N,N-dimethylaniline, N-methylpiperidine, N-methyl-morpholine, diethylamine, dicyclohexylamine, procaine, dibenzylamine, N-benzyl-b-phenethylamine, 1-ephenamine, N,N'-dibenzylethylenediamine and the like; etc.

(1) Process for Producing Compound of the General Formula [15] or its Salt

The compound of the general formula [15] or its salt can be produced by reacting a compound of the general formula [13] or its salt with a compound of the general formula [14] in the presence or absence of a base.

The solvent which is used in this reaction may be any solvent as far as it does not adversely affect the reaction, and includes, for example, aliphatic hydrocarbons such as n-hexane, cyclohexane and the like; aromatic hydrocarbons such as benzene, toluene, xylene and the like; ethers such as diethyl ether, 1,2-dimethoxyethane, tetrahydrofuran, dioxane and the like; halogenated hydrocarbons such as methylene chloride, chloroform, dichloroethane and the like; amides such as N,N-dimethylformamide, N,N-dimethylacetamide and the like; nitrites such as acetonitrile and the like; sulfoxides such as dimethylsulfoxide and the like; water; etc. These solvents may be used in admixture. Moreover, when water is used as the solvent, the use of a usually known phase transfer catalyst is effective.

The phase transfer catalyst used includes, for example, quaternary ammonium salts such as tetramethyl-ammonium bromide, tetrabutylammonium bromide, tetrabutylammonium chloride, tetrabutylammonium hydrogensulfate and the like. When the phase transfer catalyst is used, the amount thereof used is at least 0.1 mole, preferably 0.3 to 1.0 mole, per mole of the compound of the general formula [13] or its salt.

As the base which is used, if desired, there are mentioned sodium hydroxide, potassium hydroxide, sodium hydrogencarbonate, potassium carbonate, potassium tertbutoxide, sodium hydride and the like.

The amounts of the base and the compound of the general formula [14] used is each at least equal to the molar amount of, preferably 1 to 10 moles per mole of, the compound of the general formula [13] or its salt.

This reaction may be carried out usually at 0 to 180° C. for 5 minutes to 30 hours.

The obtained compound of the general formula [15] or its salt may be used as it is without isolation in the subsequent reaction.

(2) Process for Producing Compound of the General Formula [16] or its Salt

The compound of the general formula [16] or its salt can be obtained by subjecting the compound of the general formula [15] or its salt to conventional elimination reaction of carboxyl-protecting group.

(3) Process for Producing Compound of the General Formula [17] or its Salt

The compound of the general formula [17] or its salt can be obtained by subjecting the compound of the general formula [16] or its salt to ketoesterification reaction usually known in this field.

(3-a) The compound of the general formula [17] or its salt can be obtained by activating the carboxyl group of the compound of the general formula [16] or its salt according to the method described in Angew. Chem. Int. Ed. Engl., Vol. 18, page 72 (1979), for example, by converting the carboxyl group to an active acid amide form or the like using N,N'-carbonyldiimidazole, and thereafter reacting the activated species with a magnesium salt of a malonic acid monoester.

The solvent which is used in this reaction is not particularly limited as far as it does not adversely affect the reaction, and includes, for example, aromatic hydrocarbons such as benzene, toluene, xylene and the like; ethers such as dioxane, tetrahydrofuran, diethyl ether and the like; halogenated hydrocarbons such as methylene chloride, chloroform, dichloroethane and the like; and amides such as N,N-dimethylformamide, N,N-dimethylacetamide and the like. These solvents may be used in admixture.

The amount of the magnesium salt of a malonic acid monoester used is at least equal to the molar amount of, preferably 1 to 2 moles per mole of, the compound of the general formula [16] or its salt.

This reaction may be carried out at usually 0 to 100° C., preferably 10 to 80° C., for 5 minutes to 30 hours.

(3-b) Alternatively, the compound of the general formula [17] or its salt can be obtained by, for example, converting the carboxyl group of the compound of the general formula [16] or its salt to an acid halide using a halogenating agent such as thionyl chloride or the like, thereafter reacting the acid halide with a salt of a malonic acid diester with a metal such as sodium, ethoxymagnesium or the like, and then subjecting the reaction product to partial removal of the carboxyl-protecting group and decarbonization reaction using p-toluenesulfonic acid or trifluoroacetic acid in a water-containing solvent.

The solvent which is used in the reaction of the acid halide with the metal salt of a malonic acid diester is not particularly limited as far as it does not adversely affect the reaction, and specifically includes the same solvents as in (3-a) above.

The amount of the metal salt of a malonic acid diester used is at least equal to the molar amount of, preferably 1 to 3 moles per mole of, the compound of the general formula [16] or its salt.

This reaction may be carried out usually at −50 to 100° C. for 5 minutes to 30 hours.

(4) Process for Producing Compound of the General Formula [19] or its Salt (4-a) The compound of the general formula [19] or its salt can be obtained by reacting the compound of the general formula [17] or its salt with an orthoester such as methyl orthoformate, ethyl orthoformate or the like in acetic anhydride and thereafter reacting the reaction product with a compound of the general formula [18] or its salt.

The solvent which is used in this reaction is not particularly limited as far as it does not adversely affect the reaction, and include, for example, aromatic hydrocarbons such as benzene, toluene, xylene and the like; ethers such as dioxane, tetrahydrofuran, anisole, diethylene glycol diethyl ether, methyl Cellosolve and the like; alcohols such as methanol, ethanol, propanol and the like; halogenated hydrocarbons such as methylene chloride, chloroform, dichloroethane and the like; amides such as N,N-dimethylformamide, N,N-dimethylacetamide and the like; sulfoxides such as dimethyl sulfoxide and the like; etc. These solvents may be used in admixture.

The amount of the orthoester used is at least equal to the molar amount of, preferably 1 to 10 moles per mole of, the compound of the general formula [17] or its salt. These reactions may be carried out at usually 0 to 150° C., preferably 50 to 150° C., for 20 minutes to 50 hours.

In order to subsequently react the compound of the general formula [18] or its salt, it is sufficient to use this compound of the general formula [18] or its salt in an amount at least equal to the molar amount of the compound of the general formula [17] or its salt and it is sufficient to carry out the reaction at usually 0 to 100° C., preferably 10 to 60° C., for 20 minutes to 30 hours.

(4-b) Alternatively, the compound of the general formula [19] or its salt can also be derived by reacting the compound of the general formula [17] or its salt with an acetal such as N,N-dimethylformamide dimethyl acetal, N,N-dimethylformamide diethylacetal or the like in the presence or absence of an acid anhydride such as acetic anhydride or the like and thereafter reacting the reaction product with the compound of the general formula [18] or its salt.

When the acid anhydride is used, the amount thereof used is at least equal to the molar amount of, preferably 1 to 5 moles per mole of, the compound of the general formula [17] or its salt.

The solvent which is used in this reaction is not particularly limited as far as it does not adversely affect the reaction, and specifically includes the same solvents as in (4-a) above.

The amount of the acetal used is at least equal to the molar amount of, preferably about 1 to 5 moles per mole of, the compound of the general formula [17] or its salt.

These reactions may be carried out at usually 0 to 100° C., preferably 20 to 85° C., for 20 minutes to 50 hours.

In order to subsequently react the compound of the general formula [18] or its salt, it is sufficient to use this compound of the general formula [18] or its salt in an amount at least equal to the molar amount of the compound of the general formula [17] or its salt and it is sufficient to carry out the reaction at usually 0 to 100° C., preferably 10 to 60° C. for 20 minutes to 30 hours.

(5) Process for Producing Compound of the General Formula [3a] or its Salt

The compound of the general formula [3a] or its salt can be obtained by subjecting a compound of the general formula [19] or its salt to ring-closing reaction in the presence or absence of a fluoride salt or a base.

The solvent which is used in this reaction is not particularly limited as far as it does not adversely affect the reaction, and includes, for example, amides such as N,N-dimethylformamide, N,N-dimethylacetamide and the like; ethers such as dioxane, anisole, diethylene glycol dimethyl ether, dimethyl Cellosolve and the like; sulfoxides such as dimethyl sulfoxide and the like; water; etc. These solvents may be used in admixture.

The fluoride salt which is used, if desired, in this reaction includes, for example, sodium fluoride, potassium fluoride and the like.

The base which is used, if desired, in this reaction includes, for example, sodium hydroxide, potassium hydroxide, sodium hydrogencarbonate, potassium carbonate, potassium tert-butoxide, sodium hydride and the like.

The amounts of the fluoride salt and base used is each at least equal to the molar amount of, preferably 1.0 to 3.0 moles per mole of, the compound of the general formula [19] or its salt. This reaction may be carried out usually at 0 to 180° C. for 5 minutes to 30 hours.

The obtained compound of the general formula [3a] or its salt may be used as it is without isolation in the subsequent reaction.

The thus obtained compound of the general formula [3a] or its salt can be converted to the other compounds of the general formula [3a] or their salts by subjecting the former to protection reaction and/or deprotection reaction.

When the salts of the compounds of the general formulas [3a] and [13] to [19] or their salts in the above-mentioned production process have isomers (for example, optical isomers, geometrical isomers, tautomers and the like), these isomers can be used, and solvates, hydrates and crystals of various forms can also be used.

Furthermore, when the compounds of the general formulas [3a] and [13] to [19] or their salts have an amino group, a hydroxyl group or a carboxyl group, it is possible to previously protect these groups with a conventional protecting group and remove the protecting group after the reaction in a manner known per se.

Next, a process for producing a compound of the general formula [1b] or its salt using the compound of the general formula [3a] or its salt as the starting material is explained.

Production Process IVB

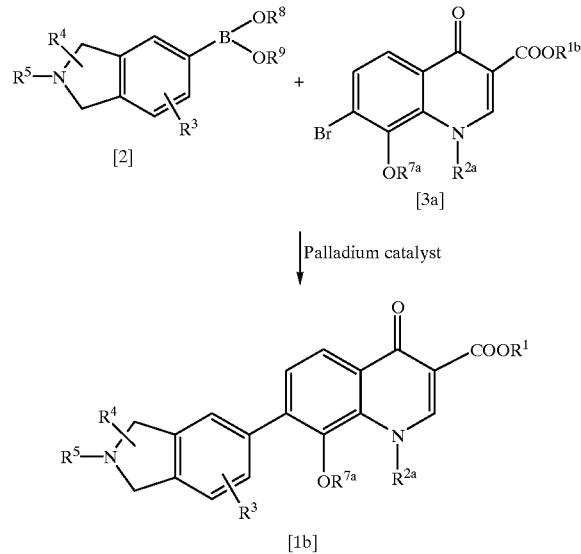

wherein $R^1$, $R^{1b}$, $R^{2a}$, $R^3$, $R^4$, $R^5$, $R^{7a}$, $R^8$ and $R^9$ have the same meanings as mentioned above.

The compound of the general formula [1b] or its salt can be produced by subjecting the compound of the general formula [2] or its salt and the compound of the general formula [3a] or its salt to coupling reaction using a palladium catalyst in the presence or absence of a base.

The solvent which is used in this reaction is not particularly limited as far as it does not adversely affect the reaction, and includes, for example, water; alcohols such as methanol, ethanol, propanol and the like; aromatic hydrocarbons such as benzene, toluene, xylene and the like; halogenated hydrocarbons such as methylene chloride, chloroform, dichloroethane and the like; ethers such as dioxane, tetrahydrofuran, anisole, diethylene glycol diethyl ether, dimethyl Cellosolve and the like; esters such as ethyl acetate, butyl acetate and the like; ketones such as acetone, methyl ethyl ketone and the like; nitriles such as acetonitrile and the like; amides such as N,N-dimethylformamide, N,N-dimethylacetamide and the like; sulfoxides such as dimethyl sulfoxide and the like; etc. These solvents may be used in admixture.

The base which is used, if desired, in this reaction includes, for example, sodium hydrogencarbonate, sodium carbonate, potassium carbonate, triethylamine and the like.

The palladium catalyst which is used in this reaction includes, for example, metallic palladiums such as palladium-activated carbon, palladium black and the like; inorganic palladium salts such as palladium chloride and the like; organic palladium salts such as palladium acetate and the like; and organic palladium complexes such as tetrakis(triphenylphosphine)palladium(0), bis(triphenylphosphine)palladium(II) chloride, 1,1'-bis(diphenylphosphino)ferrocenepalladium(II) chloride and the like.

The amount of the palladium catalyst used is at least 0.01% by mole, preferably 0.1 to 1.0% by mole, based on the amount of the compound of the general formula [3a] or its salt.

The amount of the compound of the general formula [2] or its salt used is at least equal to the molar amount of, preferably 1.0 to 1.5 moles per mole of, the compound of the general formula [3a] or its salt.

This coupling reaction may be carried out usually in an atmosphere of an inert gas (for example, argon, nitrogen) at 50 to 170° C. for 1 minute to 24 hours.

The salts of the compound of the general formula [1b] include the same salts as the above-mentioned salts of the compounds of the general formulas [3a] and [13] to [19].

The compound of the general formula [2] or its salt can be produced by, for example, the method described in WO097/29102 and the above Production Processes IB and IIA.

The salts of the compound of the general formula [2] include the same salts as the above-mentioned salts of the compounds of the general formulas [3a] and [13] to [19].

V. Salt of 7-isoindoline-3-quinolinecarboxylic Acid, Hydrate Thereof and Composition Comprising the Same as Active Ingredient In order to produce (R)-1-cyclopropyl-8-difluoromethoxy-7-(1-methyl-2,3-dihydro-1H-5-isoindolyl)-4-oxo-1,4-dihydro-3-quinolinecarboxylic acid (T-3811) methanesulfonate, it is sufficient to produce the same by a usually known process for producing a salt of a compound. Specifically, T-3811 methanesulfonate can be obtained by suspending or dissolving T-3811 in, for example, an alcohol such as methanol, ethanol or the like; N,N-dimethyl-formamide; a methanol-ether mixed solvent; or the like, adding methanesulfonic acid to the resulting suspension or solution to react with T-3811.

Moreover, T-3811 methanesulfonate can also be produced by dehydrating T-3811 methanesulfonate monohydrate in a solvent, for example, an alcohol such as methanol, ethanol or the like; N,N-dimethylformamide; a methanol-ether mixed solvent; or the like.

In order to produce T-3811 methanesulfonate monohydrate, it is sufficient to produce the same by a usually known method for producing a hydrate of salt of a compound. Specifically, T-3811 methanesulfonate monohydrate can be produced by, for example, suspending or dissolving T-3811 in a water-containing alcohol such as water-containing ethanol, water-containing isopropanol or the like; water-containing acetonitrile; water-containing acetone; water-containing tetrahydrofuran; water-containing acetic acid; water-containing N,N-dimethylformamide; water; or the like, adding methanesulfonic acid to the resulting suspension or solution to react with T-3811.

When T-3811 methanesulfonate or its monohydrate is used as an active ingredient to prepare a composition thereof with an inactive ingredient, it is preferable to prepare a preparation composition in which the inactive ingredient is a carrier acceptable as preparation.

The carrier acceptable as preparation which is used in this invention includes specifically excipients such as lactose, corn starch, crystalline cellulose, mannitol, erythritol, sucrose and the like; disintegrators such as sodium carboxymethyl starch, calcium carmellose, sodium croscarmellose, hydroxypropyl cellulose of a low substitution degree, crospovidone and the like; binders such as hydroxypropyl cellulose, povidone, methyl cellulose and the like; lubricants such as magnesium stearate, calcium stearate, talc, light anhydrous silicic acid and the like; coating agents such as hydroxypropylmethyl cellulose, ethyl cellulose, polyvinyl alcohol, methacrylic acid copolymer, hydroxypropylmethyl cellulose acetate succinate and the like; plasticizers such as macrogol, glycerine triacetate, triethyl citrate and the like; coloring agents such as iron sesquioxide, yellow iron sesquioxide, food yellow No. 5, titanium oxide and the like; sweetening agents such as sodium saccharate, aspartame, hydrogenated maltose starch and the like; viscosity improvers such as gelatine, sodium alginate and the like; tonicity agents such as mannitol, glucose, xylitol and the like; pH-adjusting agents such as methanesulfonic acid, sodium lactate solution and the like; solvents such as water for injection and the like; surface active agents such as polysorbate 80, sorbitan aliphatic acid ester, macrogol 400 and the like; ointment bases such as white vaseline, polyethylene glycol, propylene glycol, cetanol and the like; etc.

Furthermore, the amount of the T-3811 methanesulfonate or its monohydrate contained in the composition is usually 0.05 to 70% by weight, preferably 0.5 to 20% by weight, based on the weight of the composition.

The composition of this invention can be prepared in various dosage forms, for example, internal solid and liquid dosage forms such as tablet, capsule, granule, pilule, grain, powder, syrup and the like; solutions such as injection, eye drop and the like; hemi-solid dosage forms such as ointment, cream, gel, jelly and the like.

The dosage regimen, dose and number of administrations of the composition of this invention can be appropriately selected depending upon the symptom of patient, and it is usually sufficient to administer the composition in a proportion of 0.1 to 100 mg/kg per day per adult in terms of T-3811 in one to several portions.

Next, the solubility of various salts of T-3811 is explained.

[Test Method]

The solubility of each salt of T-3811 was determined by the following method:

To about 50 mg of each salt of T-3811 is added 2 ml of distilled water and they are stirred and mixed. This sample solution is exposed to ultrasonic wave irradiation 5 (SOLID STATE 1,200, Cho-onpa Kogyo) in cold water for 3 hours and then filtered through a filter with a pore size of 0.45-$\mu$m (MILLEX-HV13, MILLIPORE). The T-3811 content in this filtrate is determined by a liquid chromatography.

The results obtained are shown in Table 1.

TABLE 1

| Salt of T-3811 | pH | Solubility ($\mu$g/ml) |
|---|---|---|
| Methanesulfonate | 3.66 | 16510 |
| Phosphate | 3.29 | 8520 |
| L-lactate | 4.40 | 1980 |
| Sodium salt | 10.11 | 2340 |
| Citrate | 3.90 | 420 |
| Acetate | 4.22 | 6230 |
| Hydrochloride | 3.99 | 5450 |
| Magnesium salt | 7.58 | 60 |
| Sulfate | 3.46 | 1170 |

BEST MODE FOR CARRYING OUT THE INVENTION

Examples, Reference Examples, Production Examples and Preparation Examples are shown below to specifically explain this invention. However, this invention should not be construed to be limited thereto.

Incidentally, the mixing ratios in eluants are all by volume, and as the carriers in the column chromatography, there was used Silica Gel 60 (70 to 230 mesh) (MERCK & CO., INC.) or BW-127ZH (manufactured by Fuji Silicia Chemical Co., Ltd.).

Moreover, the abbreviation used has the following meaning:

TFA: Trifluoroacetic acid

EXAMPLE I-1

In 5 ml of toluene is dissolved 500 mg of (R)-5-bromo-2-(2,2-dimethylpropanoyl)-1-methyl-isoindoline, and thereto are added successively 510 mg of triethylamine, 35 mg of bis(triphenylphosphine)palladium(II) chloride and 330 mg of 4,4,5,5-tetramethyl-1,3,2-dioxaborolane. Thereafter, the resulting mixture is heated under reflux for 5 hours in a nitrogen atmosphere. Subsequently, to the reaction mixture are added 480 mg of ethyl 7-bromo-1-cyclopropyl-8-difluoromethoxy-1,4-dihydro-4-oxoquinoline-3-carboxylate, 360 mg of sodium carbonate and 35 mg of bis(triphenylphosphine)palladium(II) chloride and then the resulting mixture is heated under reflux for 3 hours in a nitrogen atmosphere. The reaction mixture is added to a mixed solvent of 20 ml of ethyl acetate and 10 ml of water and the organic layer is separated. The organic layer separated is washed with saturated saline and then dried over anhydrous magnesium sulfate. The solvent is removed by distillation under reduced pressure and the residue obtained is purified by a silica gel column chromatography (eluant; hexane:ethyl acetate=1:2) to obtain 470 mg of ethyl (R)-1-cyclopropyl-8-difluoromethoxy-7-[2-(2,2-dimethylpropanoyl)-1-methyl-2,3-dihydro-1H-isoindolin-5-yl]-4-oxo-1,4-dihydro-3-quinolinecarboxylate.

IR (KBr) cm$^{-1}$: 1730, 1610

NMR (CDCl$_3$)δvalue: 0.85–1.45 (4H, m), 1.37(9H, s), 1.40(3H, d, J=6.0 Hz), 1.50(3H, t, J=7.0 Hz), 4.12(1H, m), 4.41(2H, q, J=7.0 Hz), 4.95(1H, d, J=12.0 Hz), 5.08(1H, d, J=12.0 Hz), 5.50(1H, q, J=6.0 Hz), 5.90(1H, t, J=76.0 Hz), 7.39(1H, d, J=8.0 Hz), 7.41(1H, d, J=8.0 Hz), 7.49(1H, s), 7.54(1H, d, J=8.0 Hz), 8.45(1H, d, J=8.0 Hz), 8.69(1H, s)

EXAMPLE I-2

In 10 ml of dioxane is dissolved 1 g of (R)-5-bromo-2-(2,2-dimethylpropanoyl)-1-methyl-isoindoline and thereto are added successively 1.02 g of triethylamine, 1,1'-bis(diphenylphosphino)ferrocenepalladium(II) chloride and 650 mg of 4,4,5,5-tetramethyl-1,3,2-dioxoborolane, after which the resulting mixture is heated under reflux for 2 hours in an nitrogen atmosphere. The reaction mixture is added to a mixed solvent of 30 ml of ethyl acetate and 20 ml of water and the pH is adjusted to 2 with 2 moles/liter hydrochloric acid, after which the organic layer is separated. The organic layer separated is washed with saturated saline and then dried over anhydrous magnesium sulfate. The solvent is removed by distillation under reduced pressure, and the residue obtained is purified by a silica gel column chromatography (eluant; hexane:ethyl acetate=5:1) to obtain 400 mg of (R)-2-(2,2-dimethylpropanoyl)-1-methyl-5-(4,4,5,5-tetramethyl-1,3,2-dioxoborolan-2-yl)isoindoline.

IR (KBr) cm$^{-1}$: 1740, 1620, 1360, 1145

NMR (CDCl$_3$) δvalue: 1.33(9H, s), 1.35(12H, s), 1.46 (3H, d, J=6.0 Hz), 4.93(1H, d, J=12.0 Hz), 5.00(1H, d, J=12.0 Hz), 5.46(1H, q, J=6.0 Hz), 7.25(1H, d, J=7.0 Hz), 7.71(1H, s), 7.75(1H, d, J=7.0 Hz)

EXAMPLE I-3

In 3 ml of dimethyl sulfoxide is dissolved 200 mg of (R)-5-bromo-2-(2,2-dimethylpropanoyl)-1-methyl-isoindoline and thereto are added successively 200 mg of potassium acetate, 14 mg of bis(triphenylphosphine) palladium(II) chloride and 170 mg of 4,4,5,5-tetramethyl-1,3,2-dioxaborolan-2-yl-4',4',5',5'-tetramethyl-1',3',2'-dioxaborolane, after which the resulting mixture is heated under reflux for 5 hours in a nitrogen atmosphere. The reaction mixture is added to a mixed solvent of 10 ml of ethyl acetate and 10 ml of water and then the pH is adjusted to 2 with 2 moles/liter hydrochloric acid, after which the organic layer is separated. The organic layer separated is washed with saturated saline and then dried over anhydrous magnesium sulfate. The solvent is removed by distillation under reduced pressure and the residue obtained is purified by a silica gel column chromatography (eluant; hexane:ethyl acetate=5:1) to obtain 140 mg of (R)-2-(2,2-dimethylpropanoyl)-1-methyl-5-(4,4,5,5-tetramethyl-1,3,2-dioxoborolan-2-yl)isoindoline.

EXAMPLE I-4

In 15 ml of ethanol is dissolved 2.5 g of (R)-2-(2,2-dimethylpropanoyl)-1-methyl-5-(4,4,5,5-tetramethyl-1,3,2-dioxaborolan-2-yl)isoindoline and thereto are added 2.8 g of ethyl 7-bromo-1-cyclopropyl-8-difluoromethoxy-1,4-dihydro-4-oxoquinoline-3-carboxylate and 1.1 g of sodium carbonate. Subsequently, 150 mg of 10% palladium-activated carbon is added thereto under a nitrogen atmosphere and then heated under reflux for 3 hours in the same atmosphere. After cooling the reaction mixture, a mixed solvent of 15 ml of water and 30 ml of acetone is added thereto, and the deposited crystals are collected by filtration to obtain 3.6 g of ethyl (R)-1-cyclopropyl-8-difluoromethoxy-7-[2-(2,2-dimethylpropanoyl)-1-methyl-2,3-dihydro-1H-isoindolin-5-yl]-4-oxo-1,4-dihydro-3-quinolinecarboxylate.

Reference Example I-1

In 68 ml of conc. hydrochloric acid is suspended 34 g of ethyl 1-cyclopropyl-8-difluoromethoxy-7-[2-(2,2-dimethylpropanoyl)-1-methyl-2,3-dihydro-1H-isoindolin-5-yl]-4-oxo-1,4-dihydro-3-quinolinecarboxylate, and the suspension is heated under reflux for 3 hours, after which 340 ml of water is added thereto and then 170 ml of the solvent is removed by distillation under atmospheric pressure over 3 hours. After cooling the reaction mixture, 17 ml of ethanol is added thereto and the crystals deposited are collected by filtration. The resulting (R)-1-cyclopropyl-8-difluoromethoxy-7-(1-methyl-2,3-dihydro-1H-isoindolin-5-yl)-4-oxo-1,4-dihydro-3-quinolinecarboxylic acid hydrochloride is suspended in 340 ml of water, and the suspension is adjusted to pH 7.5 with 2 moles/liter sodium hydroxide solution with cooling, after which the crystals deposited are collected by filtration to obtain 25.55 g of (R)-1-cyclopropyl-8-difluoromethoxy-7-(1-methyl-2,3-dihydro-1H-isoindolin-5-yl)-4-oxo-1,4-dihydro-3-quinolinecarboxylic acid monohydrate.

Reference Example I-2

In 192 ml of 50% ethanol is suspended 24 g of (R)-1-cyclopropyl-8-difluoromethoxy-7-(1-methyl-2,3-dihydro-1H-isoindolin-5-yl)-4-oxo-1,4-dihydro-3-quinolinecarboxylic acid monohydrate and the suspension is warmed to 40° C., after which 5.71 g of methanesulfonic acid is added thereto to form a uniform solution. Subsequently, 2.4 g of activated carbon is added to the solution and the resulting mixture is stirred at the same temperature for 10 minutes and thereafter filtered. The filtrate is concentrated and the deposited crystals are collected by filtration to obtain 26.64 g of (R)-1-cyclopropyl-8-difluoromethoxy-7-(1-methyl-2,3-dihydro-1H-isoindolin-5-yl)-4-oxo-1,4-dihydro-3-quinolinecarboxylic acid methanesulfonate monohydrate.

Reference Example II-1

In 1,300 ml of water is dissolved 130 g of sodium hydroxide and in the solution is suspended 188 g of (1R)-1-phenylethylamine, after which 287 ml of pivaloyl chloride is dropwise added to the suspension at 20° C. over 40 minutes. The resulting mixture is stirred at the same temperature for 1.5 hours and the crystals deposited are collected by filtration to obtain 289 g of N-[(1R)-1-phenylethyl]-2,2-dimethylpropanamide.

$[\alpha]_D$=97 (29° C., c=1.0, CHCl$_3$)

IR (KBr) cm$^{-1}$:$\nu_{C=O}$ 1637

NMR (CDCl$_3$) δvalue: 1.20(9H,s), 1.48(3H, d, J=6.8 Hz), 5.11(1H, m), 5.8(1H, brs), 7.31(5H, s)

EXAMPLE II-1

In 466 ml of tetrahydrofuran is dissolved 77.7 g of N-[(1R)-1-phenylethyl]-2,2-dimethylpropanamide and to this solution is dropwise added 500 ml of a n-hexane solution of n-butyllithium (1.6 M solution) at −30° C. over 30 minutes. After the dropwise addition, the temperature of the resulting mixture is elevated to 0° C. and the mixture is stirred at the same temperature for 1.5 hours and then cooled again to −30° C., after which carbon dioxide is introduced into the mixture. After the introduction, the reaction mixture is added to a mixed solvent of 500 ml of ethyl acetate and 932 ml of water and the aqueous layer is separated. To the aqueous layer is added 200 ml of methylene chloride, and then the resulting aqueous layer is adjusted to pH 3 with 6 N hydrochloric acid and then the organic layer is separated. The solvent is removed from the organic layer by distillation under reduced pressure and the residue thus obtained is dissolved in 310 ml of methanol. To this solution is added 72.6 g of methane-sulfonic acid and the resulting mixture is heated under reflux for 3 hours and then cooled to 40° C., after which 777 ml of water is dropwise added to the resulting mixture and the crystals deposited are collected by filtration to obtain 77.2 g of colorless crystals of methyl 2-{(1R)-1-[(2,2-dimethylpropanoyl)amino]ethyl}benzoate.

$[\alpha]_D$=52 (29° C., c=1.0, CHCl$_3$)

IR (KBr) cm$^{-1}$: $\nu_{C=O}$ 1722, 1639

NMR (CDCl$_3$) δvalue: 1.17(9H, s), 1.47(3H, d, J=7.1 Hz), 3.93(3H, s), 5.4–5.6(1H, m), 7.1–7.6(4H, m), 7.86 (1H, dd, J=7.1, 1.2 Hz)

EXAMPLE II-2

In 560 ml of sulfuric acid is dissolved 70 g of methyl 2-{(1R)-1-[(2,2-dimethylpropanoyl)amino]ethyl}benzoate and to this solution is added 64.2 g of sodium N-bromoisocyanurate at 0° C., after which the resulting mixture is stirred with ice-cooling for 3 hours. The reaction mixture is added to a mixed solvent of 420 ml of methylene chloride and 1,050 ml of water and the insolubles are removed by filtration and then the organic layer is separated. The organic layer obtained is washed with 0.5 N aqueous sodium hydroxide solution and then dried over anhydrous magnesium sulfate, after which the solvent is removed by distillation under reduced pressure. The residue thus obtained is recrystallized from cyclohexane to obtain 74.2 g of colorless crystals of methyl 5-bromo-2-{(1R)-1-[(2,2-dimethylpropanoyl)amino]ethyl}benzoate.

$[\alpha]_D$=53 (29° C., c=1.0, CHCl$_3$)

IR (KBr) cm$^{-1}$: $\nu_{C=O}$ 1726, 1709, 1637

NMR (CDCl$_3$) δvalue: 1.16(9H, s), 1.45(3H, d, J=7.1 Hz), 3.93(3H, s), 5.3–5.7(1H, m) 6.8–7.0(1H, m), 7.28(1H, d, J=8.3 Hz), 7.59(1H, dd, J=8.3, 2.2 Hz), 8.00(1H, d, J=2.2 Hz)

EXAMPLE II-3

In 420 ml of ethanol are suspended with ice-cooling 13.4 g of sodium borohydride and 70.0 g of methyl 5-bromo-2-{(1R)-1-[(2,2-dimethylpropanoyl)amino]ethyl}benzoate and to the suspension is added 19.6 g of calcium chloride at 0° C., after which the resulting mixture is stirred with ice-cooling for 4 hours. The reaction mixture is dropwise added to 359 ml of 1 N hydrochloric acid and then 840 ml of methylene chloride and 231 ml of water are added thereto, after which the organic layer is separated. The organic layer obtained is washed with water and then dried over anhydrous magnesium sulfate, after which the solvent is removed by distillation under reduced pressure. The residue obtained is dissolved 250 ml of diethylene glycol dimethyl ether and thereto is added 32.4 ml of triethylamine, after which 16.7 ml of methanesulfonyl chloride is dropwise added thereto with ice-cooling over 30 minutes. The resulting mixture is further stirred with ice-cooling for 30 minutes. The reaction mixture is dropwise added to 1,120 ml of water and the crystals deposited are collected by filtration to obtain 70 g of colorless crystals of 5-bromo-2-{1R)-1-[(2,2-dimethylpropanoyl)amino]ethyl}benzyl methanesulfonate.

$[\alpha]_D$=26 (26° C., c–1.0 CHCl$_3$)

IR (KBr) cm$^{-1}$: $\nu_{C=O}$ 1646

NMR (CDCl$_3$) δvalue: 1.16(9H, s), 1.47(3H, d, J=6.8 Hz), 3.04(3H, s), 5.0–5.3(1H, m), 5.22(1H, d, J=11.8 Hz), 5.60 (1H, d, J=11.8 Hz), 5.8–6.0(1H, m), 7.20(1H, d, J=9.0 Hz), 7.5–7.6(2H, m)

EXAMPLE II-4

In 200 ml of diethylene glycol dimethyl ether is dissolved 25 g of 5-bromo-2-{(1R)-1-[(2,2-dimethylpropanoyl) amino]ethyl}benzyl methanesulfonate and to this solution is added 6.73 g of sodium tert-butoxide at 0° C., after which the resulting mixture is stirred at 5° C. for 2 hours. To the reaction mixture is dropwise added 150 ml of water and the crystals deposited are collected by filtration, to obtain 16.9 g of colorless crystals of 1-[(1R)-5-bromo-1-methyl-2,3-dihydro-1H-2-isoindolyl]-2,2-dimethyl-1-propanone.

$[\alpha]_D$=92 (29° C., c=1.0, CHCl$_3$)

IR (KBr) cm$^{-1}$: $\nu_{C=O}$ 1616

NMR (CDCl$_3$) δvalue: 1.32(9H, s), 1.44(3H, d, J=6.4 Hz), 4.83(1H, d, J=14.5 Hz), 5.04(1H, d, J=14.5 Hz), 5.38 (1H, q, J=6.4 Hz), 7.0–7.5(3H, m)

EXAMPLE II-5

In 130 ml of 6 moles/liter hydrochloric acid, 16.5 g of 1-[(1R)-5-bromo-1-methyl-2,3-dihydro-1H-2-isoinodolyl]-2,2-dimethyl-1-propanone is heated under reflux for 5 hours. The reaction mixture is cooled to room temperature, then washed with toluene and thereafter neutralized with 5 moles/liter aqueous sodium hydroxide solution, after which the mixture is subjected to extraction with 81 ml of methylene chloride. The extract is dried over anhydrous magnesium sulfate and thereto are added 8 ml of triethylamine and then 15.25 g of trityl chloride, after which the resulting mixture is stirred at room temperature for 1 hour. The reaction mixture is washed with water and then the solvent is removed by distillation under reduced pressure, after which the residue thus obtained is recrystallized from isopropyl alcohol to obtain 16.7 g of pale violet crystals of (1R)-5-bromo-1-methyl-2-trityl-2,3-dihydro-1H-isoindole.

$[\alpha]_D$=92 (29° C., c=1.0, CHCl$_3$)

IR (KBr) cm$^{-1}$: $\nu_{C=O}$ 1596

NMR (CDCl₃) δvalue: 1.37(3H, d, J=6.4 Hz), 3.99(1H, d, J=16.8 Hz), 4.3–4.6(2H, m), 6.5–7.6(18H, m)

EXAMPLE II-6

In 100 ml of toluene is dissolved 10.0 g of methyl 5-bromo-2-{(1R)-1-[(2,2-dimethylpropanoyl)amino]ethyl}benzoate, and to the solution is added 3.1 g of sodium tert-butoxide, after which the resulting mixture is stirred with ice-cooling for 15 minutes. The reaction mixture is added to a mixed solvent of 150 ml of water and 100 ml of ethyl acetate and the resulting mixture is neutralized with 2 N hydrochloric acid, after which the organic layer is separated. The organic layer obtained is washed with saturated saline and then dried over anhydrous magnesium sulfate, after which the solvent is removed by distillation under reduced pressure. The residue thus obtained is recrystallized from isopropyl alcohol to obtain 5.7 g of colorless crystals of (3R)-6-bromo-3-methyl-2,3-dihydro-1H-1-isoindolone.

$[\alpha]_D$=17.7 (29° C., c=1.0, CHCl₃)

IR (KBr) cm⁻¹: $\nu_{C=O}$ 1702, 1655

NMR (CDCl₃) δvalue: 1.51(3H, d, J=6.8 Hz), 4.68(1H, q, J=6.8 Hz), 7.31(1H, d, J=7.8 Hz), 7.69(1H, dd, J=7.8, 1.7 Hz), 7.95(1H, d, J=1.7 Hz)

EXAMPLE II-7

In 1,200 ml of tetrahydrofuran are suspended with ice-cooling 60.3 g of sodium borohydride and 40.0 g of (3R)-6-bromo-3-methyl-2,3-dihydro-1H-1-isoindolone, and to the resulting suspension is added 301 g of boron trifluoride-diethyl ether complex at 0° C., after which the resulting mixture is heated under reflux for 3 hours. The reaction mixture is cooled and then added to a mixed solvent of 2,000 ml of water and 700 ml of methylene chloride and the pH is adjusted to 10 with a 5 moles/liter aqueous sodium hydroxide solution, after which the organic layer is separated. The organic layer obtained is washed with water and the solvent is removed by distillation under reduced pressure, after which the residue obtained is dissolved in 200 ml of 6 moles/liter hydrochloric acid. To the solution is added 100 ml of toluene and the resulting mixture is heated under reflux for 5 minutes. The reaction mixture is cooled and thereafter the aqueous layer is adjusted to pH 10 with 5 N aqueous sodium hydroxide solution and then subjected to extraction with 200 ml of methylene chloride. The extract is dried over anhydrous magnesium sulfate and then the solvent is removed by distillation under reduced pressure to obtain 30 g of a red oily product of (1R)-5-bromo-1-methyl-2,3-dihydro-1H-isoindole.

NMR (CDCl₃) δvalue: 1.41(3H, d, J=6.3 Hz), 2.27(1H, s), 3.8–4.6(3H, m), 7.0–7.6(3H, m)

EXAMPLE II-8

In 120 ml of ethanol is dissolved 30 g of (1R)-5-bromo-1-methyl-2,3-dihydro-1H-isoindole, and 12 ml of conc. hydrochloric acid is added to the solution, after which the solvent is removed by distillation under reduced pressure. The residue thus obtained is recrystallized from isopropyl alcohol to obtain 27.7 g of red crystals of (1R)-5-bromo-1-methyl-2,3-dihydro-1H-isoindole hydrochloride.

$[\alpha]_D$=12.8 (27° C., c=1.00, CHCl₃)

IR (KBr) cm⁻¹: 1602, 1593

EXAMPLE II-9

In 32 ml of methylene chloride is suspended 3.2 g of (1R)-5-bromo-1-methyl-2,3-dihydro-1H-isoindole hydrochloride and to the suspension is added 3.94 ml of triethylamine, after which a solution of 3.95 g of trityl chloride in 10 ml of methylene chloride is added thereto and the resulting mixture is stirred at room temperature for 2 hours. The reaction mixture is washed with water and then the solvent is removed by distillation under reduced pressure, after which the residue thus obtained is recrystallized from isopropyl alcohol to obtain 4.83 g of pale violet crystals of (1R)-5-bromo-1-methyl-2-trityl-2,3-dihydro-1H-isoindole. The physical property values of this compound were identical with those of the compound obtained in Examples II-5.

EXAMPLE II-10

In 67.5 ml of tetrahydrofuran is dissolved 13.5 g of (1R)-5-bromo-1-methyl-2-trityl-2,3-dihydro-1H-isoindole and to this solution is dropwise added 19.7 ml of an n-hexane solution of n-butyllithium (1.66 M solution) at −50° C. over 10 minutes. At the same temperature, the resulting mixture is stirred for 45 minutes and thereafter 5.87 g of triisopropyl borate is dropwise added thereto over 15 minutes, after which the resulting mixture is further stirred at the same temperature for 1 hour. The reaction mixture is added to 67.5 ml of water and the resulting mixture is stirred at 10° C. for 1 hour and then adjusted to pH 7 with acetic acid, after which the organic layer is separated and dried over anhydrous magnesium sulfate. Thereafter, the solvent is removed from the dried layer by distillation under reduced pressure. The residue thus obtained is recrystallized from cyclohexane to obtain 8.6 g of brownish gray crystals of (1R)-1-methyl-2-trityl-2,3-dihydro-1H-5-isoindolylboronic acid.

$[\alpha]_D$=59 (28° C., c=1.0, CHCl₃)

IR (KBr) cm⁻¹: $\nu_{B-O}$ 1356

NMR (CDCl₃) δvalue: 1.40(3H, d, J=6.3 Hz), 4.1–4.8 (3H, m), 6.6–7.8(18H, m)

EXAMPLE II-11

In a mixed solvent of 4 ml of tetrahydrofuran and 1.5 ml of hexane is suspended 1 g of (1R)-1-methyl-2-trityl-2,3-dihydro-1H-5-isoindolylboronic acid and then 0.24 g of diethanolamine is added to the suspension, after which the resulting mixture is stirred for 20 minutes. The crystals deposited are collected by filtration to obtain 0.88 g of colorless crystals of 2-[(1R)-1-methyl-2-trityl-2,3-dihydro-1H-5-isoindolyl]-1,3,6,2-dioxazaborocane.

$[\alpha]_D$=57.2 (25° C., c=0.33, CHCl₃)

IR (KBr) cm⁻¹: 1490, 1446

NMR (CDCl₃) δvalue: 1.18(3H, d, J=6.1 Hz), 2.4–4.6 (12H, m), 6.5–7.8 (18H, m)

Production Example II-1

In a mixed solvent of 2 ml of water and 5 ml of ethyl acetate is suspended 1.34 g of 2-[(1R)-1-methyl-2-trityl-2,3-dihydro-1H-5-isoindolyl]-1,3,6,2-dioxazaborocane and to this suspension are added 1.0 g of ethyl 7-bromo-1-cyclopropyl-8-difluoromethoxy-1,4-dihydro-4-oxoquinoline-3-carboxylate, 0.55 g of sodium carbonate and 0.05 g of bis(triphenylphosphine)palladium(II) chloride, after which the resulting mixture is heated under reflux for 3 hours in a nitrogen atmosphere. The reaction mixture is added to a mixed solvent of 10 ml of methylene chloride and 10 ml of water, and the organic layer is separated. The organic layer obtained is washed with saturated saline and then dried over anhydrous magnesium sulfate, after which the solvent is removed by distillation under reduced pressure. The residue thus obtained is recrystallized from ethanol to obtain 1.55 g of ethyl 1-cyclopropyl-8-difluoromethoxy-7-[(1R)-1-methyl-2-trityl-2,3-dihydro-1H-5-isoindolyl]-4-oxo-1,4-dihydro-3-quinolinecarboxylate.

$[\alpha]_D$=32 (27° C., c=1.0, CHCl$_3$)

IR (KBr) cm$^{-1}$: $v_{C=O}$ 1734, 1690

NMR (CDCl$_3$) δvalue: 0.8–1.9(10H, m), 3.9–4.9(6H, m), 5.51(1H, t, J=75 Hz), 6.7–8.0(19H, m), 8.35(1H, d, J=8.0 Hz), 8.66(1H, s)

Production Example II-2

In a mixed solvent of 50.6 ml of water and 50.6 ml of diethylene glycol dimethyl ether is suspended 13.5 g of 2-[(1R)-1-methyl-2-trityl-2,3-dihydro-1H-5-isoindolyl]-1,3,6,2-dioxazaborocane and to this suspension is added 1.58 ml of acetic acid, after which the resulting mixture is stirred for 30 minutes. To this mixture are further added 10.1 g of ethyl 7-bromo-1-cyclopropyl-8-difluoromethoxy-1,4-dihydro-4-oxoquinoline-3-carboxylate, 5.59 g of sodium carbonate and 0.088 g of bis(triphenylphosphine)palladium(II) chloride, and the resulting mixture is heated under reflux for 2 hours in a nitrogen atmosphere. The reaction mixture is cooled to 40° C. and thereafter the organic layer is separated. To the organic layer obtained is added 30 ml of ethanol and the crystals deposited are collected by filtration to obtain 17.3 g of ethyl 1-cyclopropyl-8-difluoromethoxy-7-[(1R)-1-methyl-2-trityl-2,3-dihydro-1H-5-isoindolyl]-4-oxo-1,4-dihydro-3-quinolinecarboxylate. The physical property values of this compound were identical with those of the compound obtained in Production Example II-1.

EXAMPLE III-1

In 495 ml of water is dissolved 83.7 g of sodium hydroxide and to this solution are added 165 g of R-(+)-1-(4-bromophenyl)ethylamine hydrochloride and 495 ml of isopropanol, after which 92.5 g of pivaloyl chloride is dropwise added to the resulting solution at 20° C. over 1.5 hours. At the same temperature, the resulting mixture is stirred for 30 minutes, and thereafter, 660 ml of water is dropwise added to the mixture over 30 minutes, after which the resulting mixture is cooled to 10° C. The mixture is stirred at the same temperature for 1 hour and thereafter the deposits are collected by filtration to obtain 193.5 g (yield: 97.6%) of colorless crystals of N-[(1R)-1-(4-bromophenyl)ethyl]-2,2-dimethylpropanamide.

Melting point: 132–134° C.

$[\alpha]_D$+92° (25° C., c=1.0, CHCl$_3$)

IR (KBr) cm$^{-1}$: $v_{C=O}$ 1636

NMR (CDCl$_3$) δvalue: 1.19(9H, s), 1.45(3H, d, J=6.8 Hz), 4.90–5.20(1H, m), 5.70–6.00(1H, m), 7.16(2H, d, J=8.5 Hz), 7.45(2H, d, J=8.5 Hz)

EXAMPLE III-2

In 10 ml of tetrahydrofuran is dissolved 2 g of N-[(1R)-1-(4-bromophenyl)ethyl]-2,2-dimethylpropanamide, and to this solution is dropwise added 14.3 ml of phenyllithium (1.48 M cyclohexane-diethyl ether solution), after which the temperature of the resulting mixture is elevated to –5° C. and the mixture is stirred at the same temperature for 4 hours. Subsequently, 1.06 g of paraformaldehyde is added thereto and the mixture is stirred at 5° C. for 1 hour, after which 6 ml of water is added to the reaction mixture and the organic layer is separated. The organic layer obtained is dried over anhydrous magnesium sulfate and the solvent is removed by distillation under reduced pressure. The residue obtained is purified by silica gel chromatography (eluant; n-hexane:ethyl acetate=2:1) to obtain 1.48 g (yield: 66.9%) of 5-bromo-2-{(1R)-1-[(2,2-dimethylpropanoyl)amino]ethyl}benzyl alcohol.

IR (KBr) cm$^{-1}$: $v_{C=O}$ 1639, 1610

NMR (CDCl$_3$) δvalue: 1.14(9H, s), 1.46(3H, d, J=6.8 Hz), 4.3–5.4(4H, m), 6.0–6.4(1H, m), 7.0–7.6(3H, m)

EXAMPLE III-3

In 135 ml of methylene chloride is dissolved 13.50 g of 5-bromo-2-{(1R)-1-[(2,2-dimethylpropanoyl)amino]ethyl}benzyl alcohol, and to this solution are added with ice-cooling 6.59 ml of triethylamine and 3.66 ml of methanesulfonyl chloride, after which the resulting mixture is stirred with ice-cooling for 1 hour. Subsequently, 50 ml of water is added to the reaction mixture and the pH is adjusted to 2.0 with 2 moles/liter hydrochloric acid and thereafter the organic layer is separated. The organic layer obtained is washed with water and then dried over anhydrous magnesium sulfate, after which the solvent is removed by distillation under reduced pressure. To the residue obtained are added 50 ml of toluene and 50 ml of cyclohexane, and the deposits are collected by filtration to obtain 11.5 g (yield: 68.2%) of colorless crystals of 5-bromo-2-{(1R)-1-[(2,2-dimethylpropanoyl)amino]ethyl}benzyl methanesulfonate.

$[\alpha]_D$+26° (25° C., c=1.0, CHCl$_3$)

IR (KBr) cm$^{-1}$: vC=O 1646

NMR (CDCl$_3$) δvalue: 1.16(9H, s), 1.47(3H, d, J=6.8 Hz), 3.04(3H, s), 5.0–5.3(1H, m), 5.22(1H, d, J=11.8 Hz), 5.60 (1H, d, J=11.8 Hz), 5.8–6.0(1H, m), 7.20(1H, d, J=9.0 Hz), 7.5–7.6(2H, m)

EXAMPLE III-4

In 225 ml of tetrahydrofuran is dissolved 45 g of N-[(1R)-1-(4-bromophenyl)ethyl]-2,2-dimethylpropanamide, and to this solution is dropwise added 505 ml of phenyllithium (0.94 M cyclohexane-diethyl ether solution) at –30° C., after which the temperature of the mixture is elevated to –5° C. and the mixture is stirred at the same temperature for 3 hours. Subsequently, 23.77 g of paraformaldehyde is added to the mixture and the resulting mixture is stirred at 5° C. for 1 hour, after which 180 ml of water is added to the reaction mixture and the organic layer is separated. The organic layer obtained is washed with saturated saline and then dried over Zeolum 4A (manufactured by TOSOH CORP.), after which Zeolum 4A is removed by filtration. To the filtrate obtained is added 43.26 g of triethylamine and the resulting mixture is cooled to 10° C., after which 31.07 g of acetyl chloride is dropwise added to the mixture over 30 minutes. The resulting mixture is stirred at the same temperature for 25 minutes. Subsequently, 180 ml of water is added to the reaction mixture and then the pH is adjusted to 2.0 with 2 moles/liter hydrochloric acid, after which the organic layer is separated. The organic layer obtained is washed successively with 5% (w/w) sodium hydrogencarbonate and water, and thereafter, the solvent is removed by distillation under atmospheric pressure. To the residue obtained are added 113 ml of cyclohexane and 135 ml of n-hexane and the deposits are collected by filtration to obtain 33.93 g (yield: 60.1%) of colorless crystals of 5-bromo-2-{(1R)-1-[(2,2-dimethylpropanoyl)amino]ethyl}benzyl acetate.

Melting point: 109–112.5° C.

IR (KBr) cm$^{-1}$: $v_{C=O}$ 1750, 1734, 1635

NMR (CDCl$_3$) δvalue: 1.17(9H, s), 1.45(3H, d, J=6.8 Hz), 2.10(3H, s), 4.90–5.50(3H, m), 5.70–6.10(1H, m), 7.10–7.60(3H, m)

EXAMPLE III-5

In 20 ml of tetrahydrofuran is dissolved 4.0 g of N-[(1R)-1-(4-bromophenyl)ethyl]-2,2-dimethylpropanamide, and to this solution is dropwise added 45 ml of phenyllithium (0.94 M cyclohexane-diethyl ether solution) at −30° C., after which the temperature of the resulting mixture is elevated to −5° C. and the mixture is stirred at the same temperature for 2 hours. Subsequently, 1.69 g of paraformaldehyde is added to the mixture and the resulting mixture is stirred at 5° C. for 1 hour, after which 160 ml of water is added to the reaction mixture and the organic layer is separated. The organic layer obtained is washed with saturated saline and then dried with Zeolum 4A, after which Zeolum 4A is removed from the layer by filtration. The filtrate obtained is cooled to −15° C. and then 2.10 ml of thionyl chloride is added to the filtrate, after which the temperature of the resulting mixture is elevated to room temperature and the mixture is stirred at the same temperature for 1 hour. Subsequently, 8 ml of water is added to the reaction mixture and the pH is adjusted to 5.5 with 5 moles/liter sodium hydroxide solution, after which the organic layer is separated. The organic layer obtained is subjected to removal of the solvent by distillation under atmospheric pressure and to the residue obtained are added 12 ml of cyclohexane and 12 ml of n-hexane and then the deposits are collected by filtration to obtain 2.43 g (yield 52.0%) of colorless crystals of 5-bromo-2-{(1R)-1-[(2,2-dimethylpropanoyl)amino]ethyl}benzyl chloride.

IR (KBr) cm$^{-1}$: $v_{C=O}$ 1634

NMR (CDCl$_3$) δvalue: 1.16(9H, s), 1.49(3H, d, J=6.8 Hz), 4.48(1H, d, J=11.7 Hz), 5.07(1H, d, J=11.7 Hz), 5.00–5.40 (1H, m), 5.70–6.10(1H, m), 7.10–7.60(3H, m)

EXAMPLE III-6

To a mixed solution of 30 g of a 50% (w/w) aqueous sodium hydroxide solution and 40 ml of toluene are added 10 g of 5-bromo-2-{(1R)-1-[(2,2-dimethylpropanoyl) amino]ethyl}benzyl acetate and 0.27 g of tetra-n-butylammonium bromide at room temperature, and the temperature of the resulting mixture is elevated to 35° C., after which the mixture is stirred for 1 hour. The mixture is cooled to room temperature and thereafter 30 ml of water is added to the reaction mixture, after which the organic layer is separated. The organic layer is dried over anhydrous magnesium sulfate and then the anhydrous magnesium sulfate is removed by filtration. To the filtrate obtained is added 3.98 g of triethylamine and the resulting mixture is cooled to 10° C., after which 3.86 g of methanesulfonyl chloride is dropwise added thereto over 10 minutes. At the same temperature, the mixture is stirred for 30 minutes and thereafter 30 ml of water is added to the reaction mixture, after which the organic layer is separated. To the organic layer obtained is added 30 g of a 50% (w/w) aqueous sodium hydroxide solution and the temperature of the resulting mixture is elevated to 35° C., after which 0.27 g of tetra-n-butylammonium bromide is added thereto. The mixture is stirred at the same temperature for 1 hour and 35 minutes and then cooled to room temperature, after which 30 ml of water is added to the reaction mixture and the organic layer is separated. The organic layer separated is washed with water and thereafter the solvent is removed by distillation under reduced pressure, after which to the residue obtained are added 10 ml of ethylene glycol and 20 ml of conc. hydrochloric acid. The resulting mixture is heated under reflux for 4 hours. After cooling, to the reaction mixture are added 40 ml of water and 20 ml of toluene and then the aqueous layer is separated. The aqueous layer obtained is treated with active carbon and thereto is then added 40 ml of methylene chloride, after which the pH is adjusted to 11 with 20% (w/w) aqueous sodium hydroxide solution. Subsequently, the organic layer is separated and dried over anhydrous magnesium sulfate and thereafter to the organic layer is added 2.98 g of triethylamine, after which the resulting mixture is cooled to −15° C. and then 7.43 g of trityl chloride is added thereto. The temperature of the reaction mixture is elevated to room temperature and the mixture is stirred at room temperature for 30 minutes, after which 20 ml of water is added thereto and the organic layer is separated. The organic layer separated is subjected to removal of the solvent by distillation under atmospheric pressure and 45 ml of isopropanol is added to the residue obtained, after which the deposits were collected by filtration to obtain 10.11 g (yield: 79.0%) of pale violet crystals of (1R)-5-10 bromo-1-methyl-2-trityl-2,3-dihydro-1H-isoindole.

[α]$_D$+92°(25° C., c=1.0, CHCl$_3$)

IR (KBr) cm$^{-1}$: 1596

NMR (CDCl$_3$) δvalue: 1.37(3H, d, J=6.4 Hz), 3.99(1H, d, J=16.8 Hz), 4.3–4.6(2H, m), 6.5–7.6(18H, m)

EXAMPLE III-7

The same ring-closing reaction as in Example III-6 is repeated by replacing the 5-bromo-2-{(1R)-1-[(2,2-dimethylpropanoyl)amino]ethyl}benzyl acetate by 5-bromo-2-{(1R)-1-[(2,2-dimethylpropanoyl)amino] ethyl}benzyl chloride to obtain (1R)-5-bromo-1-methyl-2-trityl-2,3-dihydro-1H-isoindole.

EXAMPLE III-8

In 230 ml of tetrahydrofuran is dissolved 46 g of N-[(1R)-1-(4-bromophenyl)ethyl]-2,2-dimethylpropanamide, and to this solution is dropwise added 300 ml of phenyllithium (1.62 M cyclohexane-diethyl ether solution) at −35° C. and the temperature of the resulting mixture is elevated to −5° C., after which the mixture is stirred at the same temperature for 2 hours. Subsequently, 19.46 g of paraformaldehyde is added to the mixture and the resulting mixture is stirred at 5° C. for 1 hour, after which 138 ml of water is added to the reaction mixture, and the organic layer is separated. The organic layer obtained is dried with Zeolum 4A and then Zeolum 4A is removed by filtration. To the filtrate obtained are added 40.95 g of triethylamine and 37.10 g of methanesulfonyl chloride at 10° C. and the resulting mixture is stirred at the same temperature for 30 minutes. Subsequently, 92 ml of water is added to the reaction mixture and the pH is adjusted to 2.5 with 6 moles/liter hydrochloric acid, after which the organic layer is separated. To the organic layer separated are added 138 g of 50% (w/w) aqueous sodium hydroxide solution and 4.6 g of tetra-n-butylammonium bromide and the resulting mixture is stirred at 20° C. for 2 hours, after which 92 ml of water is added to the reaction mixture and the organic layer is separated. To the organic layer obtained is added 92 ml of water and the pH is adjusted to 3.0 with 6 moles/liter hydrochloric acid, after which the solvent is removed by distillation under atmospheric pressure. To the residue obtained are added 46 ml of ethylene glycol and 92 ml of conc. hydrochloric acid, and the resulting mixture is heated under reflux for 6 hours. After cooling, to the reaction mixture are added 138 ml of water and 92 ml of toluene, and the aqueous layer is separated. The aqueous layer is treated with active carbon and thereafter 138 ml of methylene chloride is added thereto, after which the pH is adjusted to 11 with 5 moles/liter aqueous sodium hydroxide solution. Subsequently, the organic layer is separated and dried over Zeolum 4A. To the organic layer obtained is added 13.10 g of triethylamine and the resulting mixture is cooled to −15° C. and then 31.59 g of trityl chloride is added thereto. The temperature of the reaction mixture is elevated to room temperature and the mixture is stirred at room temperature for 30 minutes, after which 138 ml of water is added thereto and the organic layer is separated. The organic layer separated is subjected to removal of the solvent by distillation under atmospheric pressure and to the residue obtained is added 207 ml of isopropanol and the deposits are collected by filtration to obtain 42.5 g (yield: 57.7%) of pale violet crystals of (1R)-5-bromo-1-methyl-2-trityl-2,3-dihydro-1H-isoindole. The physical property values of this compound were identical with those of the compound obtained in Example III-6.

Production Example III-1

In 67.5 ml of tetrahydrofuran is dissolved 13.5 g of (1R)-5-bromo-1-methyl-2-trityl-2,3-dihydro-1H-isoindole, and to this solution is dropwise added 19.7 ml of an n-hexane solution of n-butyllithium (1.66 M solution) at −50° C. over 10 minutes. At the same temperature, the resulting mixture is stirred for 45 minutes and thereafter 5.87 g of triisopropyl borate is dropwise added to the mixture over 15 minutes, after which the mixture is stirred at the same temperature for 1 hour. The reaction mixture is added to 67.5 ml of water and the resulting mixture is stirred at 10° C. for 1 hour, after which the pH is adjusted to 7 with acetic acid and the organic layer is separated. The organic layer separated is dried over anhydrous magnesium sulfate and thereafter the solvent is removed from the layer by distillation under reduced pressure. The residue obtained is recrystallized from cyclohexane to obtain 8.6 g of brownish gray crystals of (1R)-1-methyl-2-trityl-2,3-dihydro-1H-5-isoindolylboronic acid.

$[\alpha]_D$+590 (28° C., c=1.0, CHCl$_3$)

IR (KBr) cm$^{-1}$: $v_{B=O}$ 1356

NMR (CDCl$_3$) δvalue: 1.40(3H, d, J=6.3 Hz), 4.1–4.8 (3H, m), 6.6–7.8(18H, m)

Production Example III-2

In a mixed solvent of 4 ml of tetrahydrofuran and 1.5 ml of hexane is suspended 1 g of (1R)-1-methyl-2-trityl-2,3-dihydro-1H-5-isoindolylboronic acid and then 0.24 g of diethanolamine is added to the suspension, after which the resulting mixture is stirred for 20 minutes. The deposits are collected by filtration to obtain 0.88 g of colorless crystals of 2-[(1R)-1-methyl-2-trityl-2,3-dihydro-1H-5-isoindolyl]-1,3,6,2-dioxazaborocane.

$[\alpha]_D$ +57.20 (25° C., c=0.33, CHCl$_3$)

IR (KBr) cm$^{-1}$: 1490, 1446

NMR (CDCl$_3$) δvalue: 1.18(3H, d, J=6.1 Hz), 2.4–4.6 (12H, m), 6.5–7.8(18H, m)

Production Example III-3

In a mixed solvent of 2 ml of water and 5 ml of ethyl acetate is suspended 1.34 g of 2-[(1R)-1-methyl-2-trityl-2,3-dihydro-1H-5-isoindolyl]-1 3,6,2-dioxazaborocane and to this suspension are added 1.0 g of ethyl 7-bromo-1-cyclopropyl-8-difluoromethoxy-1,4-dihydro-4-oxoquinoline-3-carboxylate, 0.55 g of sodium carbonate and 0.05 g of bis(triphenylphosphine)palladium(II) chloride, after which the resulting mixture is heated under reflux for 3 hours in a nitrogen atmosphere. The reaction mixture is added to a mixed solvent of 10 ml of methylene chloride and 10 ml of water and the organic layer is separated. The organic layer obtained is washed with saturated saline and then dried over anhydrous magnesium sulfate, after which the solvent is removed from the layer by distillation under reduced pressure. The residue obtained is recrystallized from ethanol to obtain 1.55 g of ethyl 1-cyclopropyl-8-difluoromethoxy-7-[(1R)-1-methyl-2-trityl-2,3-dihydro-1H-5-isoindolyl]-4-oxo-1,4-dihydro-3-quinolinecarboxylate.

$[\alpha]_D$+320 (27° C., c=1.0, CHCl$_3$)

IR (KBr) cm$^{-1}$; $v_{C=O}$ 1734, 1690

NMR (CDCl$_3$) δvalue: 0.8–1.9(10H, m), 3.9–4.9(6H, m), 5.51(1H, t, J=75 Hz), 6.7–8.0(19H, m), 8.35(1H, d, J=8.0 Hz), 8.66(1H, s)

Reference Example IV-1

To a mixed solvent of 193.3 g of bromine and 600 ml of methylene chloride is dropwise added 176.1 g of tert-butylamine at −20° C. over 1 hour and the resulting mixture is stirred at the same temperature for 1 hour, after which 100.0 g of ethyl m-hydroxybenzoate is added to the mixture in 5 portions. The resulting mixture is stirred at the same temperature for 2 hours, then at 0° C. for 1 hour and further at room temperature for 10 hours. The deposited matters are collected by filtration and to the matters obtained are added 500 ml of ethyl acetate and 300 ml of 6 moles/liter hydrochloric acid, and the organic layer is separated. The organic layer is washed with saturated saline and then dried over anhydrous magnesium sulfate, and the solvent is removed by distillation under reduced pressure. The residue obtained is purified by distillation under reduced pressure (135–142° C./0.5 mmHg) to obtain 121.0 g of a colorless oily product of ethyl 2,4-dibromo-3-hydroxybenzoate.

IR (KBr) cm$^{-1}$: $v_{C=O}$ 1722

NMR (CDCl$_3$) δvalue: 1.40(3H, t, J=7.1 Hz), 4.40(2H, q, J=7.1 Hz), 6.39(1H, brs), 7.26(1H, d, J=8.3 Hz), 7.52 (1H, d, J=8.3 Hz)

EXAMPLE IV-1

To a mixed solution of 400 ml of a 35% aqueous sodium hydroxide solution and 49.8 g of tetrabutylammonium bromide is added a solution of 100.0 g of ethyl 2,4 -dibromo-3-hydroxybenzoate in 400 ml of toluene and thereafter 53.4 g of chlorodifluoromethane is blown into the resulting mixture at room temperature over 1 hour. To the reaction mixture is added 400 ml of water and the organic layer is separated. The organic layer obtained is washed with saturated saline and then dried over anhydrous magnesium sulfate, and the solvent is removed by distillation under reduced pressure. The residue obtained is purified by a column chromatography [eluant; n-hexane ethyl acetate= 10:1] to obtain 110.8 g of colorless crystals of ethyl 2,4-dibromo-3-difluoromethoxybenzoate.

IR (KBr) cm$^{-1}$: vC=O 1727

NMR (CDCl$_3$) δvalue: 1.41(3H, t, J=7.1 Hz), 4.41(2H, q, J=7.1 Hz), 6.65(1H, t, J=74.8 Hz), 7.48(1H, d, J=8.3 Hz), 7.66(1H, d, J=8.3 Hz)

EXAMPLE IV-2

In 10 ml of N,N-dimethylformamide is dissolved 10.0 g of ethyl 2,4-dibromo-3-hydroxybenzoate and to the solution are added 4.5 g of potassium carbonate and then 100 ml of an N,N-dimethylformamide solution of chlorodifluoromethane (10 M solution), after which the resulting mixture is stirred at 120–130° C. for 3 hours in a sealed tube. The reaction mixture is added to a mixed solvent of 100 ml of ethyl acetate and 100 ml of water, and the pH is adjusted to 2 with 6 moles/liter hydrochloric acid, after which the organic layer is separated. The organic layer obtained is washed with saturated saline and then dried over anhydrous magnesium sulfate, and the solvent is removed by distillation under reduced pressure. The residue obtained is purified by a column chromatography [eluant; n-hexane:ethyl acetate=4:1] to obtain 10.8 g of colorless crystals of ethyl 2,4-dibromo-3-difluoro-methoxybenzoate.

IR (KBr) cm$^{-1}$: $\nu_{C=O}$ 1717

NMR (CDCl$_3$) δvalue: 6.68(1H, t, J=74.8 Hz), 7.60–7.90 (2H, m), 8.83(1H, brs)

EXAMPLE IV-3

In 600 ml of methylene chloride is dissolved 100.0 g of 2,4-dibromo-3-difluoromethoxybenzoic acid and thereto are added 21.6 g of imidazole and 96.5 g of triethylamine, after which 37.8 g of thionyl chloride is added to the resulting mixture with ice-cooling. The resulting mixture is stirred at the same temperature for 30 minutes and further at room temperature for 1 hour. Subsequently, 27.5 g of magnesium chloride, 29.3 g of triethylamine, 98.4 g of potassium monoethyl malonate and 100 ml of N,N-dimethylformamide are added successively to the mixture and the resulting mixture is heated under reflux for 6 hours. To the reaction mixture is added 600 ml of water and the pH is adjusted to 1 with 6 moles/liter hydrochloric acid, after which the organic layer is separated. The organic layer obtained is washed successively with a saturated aqueous sodium hydrogen-carbonate solution, water and saturated saline, and thereafter, dried over anhydrous magnesium sulfate, after which the solvent is removed by distillation under reduced pressure. The residue obtained is purified by a column chromatography [eluant; n-hexane:ethyl acetate=20:1] to obtain 108.2 g of colorless crystals of ethyl 2,4-dibromo-3-difluoromethoxybenzoyl acetate.

IR (KBr) cm$^{-1}$: $\nu_{C=O}$ 1670

NMR (CDCl$_3$) δvalue: 1.25(1.8H, t, J=7.1 Hz), 1.34 (1.2H, t, J=7.1 Hz), 3.98(1.2H, s), 4.19(1.2H, q, J=7.1 Hz), 4.29(0.8H, q, J=7.1 Hz), 5.40(0.4H, s), 6.65(1H, t, J=73.7 Hz), 7.25(1H, d, J=8.3 Hz), 7.65(0.6H, d, J=8.3 Hz), 7.69 (0.4H, d, J=8.3 Hz), 12.41(0.4H, s)

EXAMPLE IV-4

In 600 ml of methylene chloride is dissolved 100.0 g of ethyl 2,4-dibromo-3-difluoromethoxybenzoyl-acetate and to the solution are added 31.9 g of acetic anhydride and 37.2 g of N,N-dimethylformamide dimethyl acetal, after which the resulting mixture is stirred at room temperature for 1 hour and the solvent is removed by distillation under reduced pressure. The residue obtained is dissolved in 500 ml of isopropanol, and 14.8 g of cyclopropylamine is added thereto, after which the resulting mixture is stirred at room temperature for 1 hour. The crystals deposited are collected by filtration to obtain 95.2 g of colorless crystals of ethyl 2-(2,4-dibromo-3-difluoromethoxybenzoyl)-3-cyclopropylaminoacrylate.

IR (KBr) cm$^{-1}$: $\nu_{C=O}$ 1675, 1621

NMR (CDCl$_3$) δvalue: 0.60–1.20(7H, m), 2.80–3.20(1H, m), 3.96(2H, q, J=7.1 Hz), 6.61(1H, t, J=74.0 Hz), 6.92(1H, d, J=8.3 Hz), 7.58(1H, d, J=8.3 Hz), 8.28(0.8H, d, J=13.9 Hz), 8.37(0.2H, d, J=13.9 Hz), 9.60–9.90(0.2H, m), 10.80–11.30(0.8H, m)

EXAMPLE IV-5

In 400 ml of dimethyl sulfoxide is dissolved 100.0 g of ethyl 2-(2,4-dibromo-3-difluoromethoxybenzoyl)-3-cyclopropylaminoacrylate and then 34.3 g of potassium carbonate is added thereto, after which the resulting mixture is stirred at 90° C. for 2 hours. The reaction mixture is cooled to room temperature and thereafter 800 ml of water is added thereto, after which the crystals deposited are collected by filtration to obtain 78.3 g of colorless crystals of ethyl 7-bromo-1-cyclopropyl-8-difluoromethoxy-1,4-dihydro-4-oxoquinoline-3-carboxylate.

IR (KBr) cm$^{-1}$: $\nu_{C=O}$ 1687, 1640

NMR (CDCl$_3$) δvalue: 0.70–1.70(7H, m), 3.70–4.70(3H, m), 6.52(1H, t, J=74.5 Hz), 7.58(1H, d, J=8.5 Hz), 8.24(1H, d, J=8.5 Hz), 8.59(1H, s)

Production Example IV-1

In 15 ml of ethanol is dissolved 2.5 g of (R)-2-(2,2-dimethylpropanoyl)-1-methyl-5-(4,4,5,5-tetramethyl-1,3,2-dioxaborolan-2-yl)isoindoline, and thereto are added 2.8 g of ethyl 7-bromo-1-cyclopropyl-8-difluoromethoxy-1, 4-dihydro-4-oxoquinoline-3-carboxylate and 1.1 g of sodium carbonate. Subsequently, 150 mg of 10% palladium-activated carbon is added to the mixture in a nitrogen atmosphere and thereafter the resulting mixture is heated under reflux for 3 hours in the same atmosphere. The reaction mixture is cooled and thereafter added to a mixed solvent of 15 ml of water and 30 ml of acetone, and the crystals deposited are collected by filtration to obtain 3.6 g of ethyl (R)-1-cyclopropyl-8-difluoromethoxy-7-[2-(2,2-dimethylpropanoyl)-1-methyl-2,3-dihydro-1H-5-isoindolyl]-4-oxo-1,4-dihydro-3-quinolinecarboxylate.

Production Example IV-2

In 68 ml of conc. hydrochloric acid is suspended 34 g of ethyl (R)-1-cyclopropyl-8-difluoromethoxy-7-[2-(2,2-dimethylpropanoyl)-1-methyl-2,3-dihydro-1H-5-isoindolyl]-4-oxo-1,4-dihydro-3-quinolinecarboxylate, and the suspension is heated under reflux for 3 hours, after which 340 ml of water is added to the resulting mixture and 170 ml of the solvent is removed from the mixture by distillation under atmospheric pressure over 3 hours. The reaction mixture is cooled and thereafter 17 ml of ethanol is added to the mixture, after which the crystals deposited are collected by filtration. The resulting (R)-1-cyclopropyl-8-difluoromethoxy-7-(1-methyl-2,3-dihydro-1H-5-isoindolyl)-4-oxo-1,4-dihydro-3-quinolinecarboxylic acid hydrochloride is suspended in 340 ml of water and the pH of the mixture is adjusted to 7.5 with 2 moles/liter sodium hydroxide solution, after which the crystals deposited are collected by filtration to obtain 25.55 g of (R)-1-cyclopropyl-8-difluoromethoxy-7-(1-methyl-2,3-dihydro-1H-5-isoindolyl)-4-oxo-1,4-dihydro-3-quinolinecarboxylic acid monohydrate.

Production Example IV-3

In 192 ml of 50% ethanol is suspended 24 g of (R)-1-cyclopropyl-8-difluoromethoxy-7-(1-methyl-2,3-dihydro-1H-5-isoindolyl)-4-oxo-1,4-dihydro-3-quinolinecarboxylic acid monohydrate, and the suspension is warmed to 40° C., after which 5.71 g of methanesulfonic acid is added to form a uniform solution. Subsequently, 2.4 g of activated carbon is added and the resulting mixture is stirred at the same temperature for 10 minutes, after which the insolubles are removed by filtration. The filtrate is concentrated and the crystals deposited are collected by filtration to obtain 26.64 g of (R)-1-cyclopropyl-8-difluoromethoxy-7-(1-methyl-2,3-dihydro-1H-5-isoindolyl)-4-oxo-1,4-dihydro-3-quinolinecarboxylic acid methanesulfonate monohydrate.

EXAMPLE V-1

In 192 ml of 50% water-containing ethanol is suspended 24 g of (R)-1-cyclopropyl-8-difluoromethoxy-7-(1-methyl-2,3-dihydro-1H-5-isoindolyl)-4-oxo-1,4-dihydro-3-quinolinecarboxylic acid and the suspension is warmed to 40° C., after which 5.71 g of methanesulfonic acid is added to the warmed suspension to form a uniform solution. Subsequently, the solution is stirred at the same temperature for 10 minutes and thereafter filtered, and the filtrate is concentrated, after which the crystals deposited are collected by filtration to obtain 26.64 g of (R)-1-cyclopropyl-8-difluoromethoxy-7-(1-methyl-2,3-dihydro-1H-5-isoindolyl)-4-oxo-1,4-dihydro-3-quinolinecarboxylic acid methanesulfonate monohydrate.

IR (KBr) cm$^{-1}$: $v_{C=O}$ 1724, 1615

NMR (TFA-d) δvalue: 1.2–2.1(7H, m), 3.16(3H, s), 4.7–5.7(4H, m), 6.21(1H, t, J=72 Hz), 7.5–8.0(3H, m), 8.14(1H, d, J=10 Hz), 8.78(1H, d, J=10 Hz), 9.66 (1H, s)

Water content: 3.31%

EXAMPLE V-2

In 4 ml of ethanol is suspended 0.2 g of (R)-1-cyclopropyl-8-difluoromethoxy-7-(1-methyl-2,3-dihydro-1H-5-isoindolyl)-4-oxo-1,4-dihydro-3-quinolinecarboxylic acid and then the suspension is warmed to 70° C., after which 45 mg of methanesulfonic acid is added to the warmed suspension to form a uniform solution. Subsequently, the solution is stirred at the same temperature for 1 hour and then cooled to room temperature, after which the crystals deposited are collected by filtration to obtain 0.20 g of (R)-1-cyclo-propyl-8-difluoromethoxy-7-(1-methyl-2,3-dihydro-1H-5-isoindolyl)-4-oxo-1,4-dihydro-3-quinolinecarboxylic acid methanesulfonate.

IR(KBr) cm$^{-1}$: $\mu_{C=O}$ 1716, 1613

NMR (TFA-d) δvalue: 1.2–2.1(7H, m), 3.16(3H, s), 4.6–5.6(4H, m), 6.21(1H, t, J=73 Hz), 7.4–8.0(3H, m), 8.17(1H, d, J=10 Hz), 8.80(1H, d, J=10 Hz), 9.66(1H, s)

Water content: 0.1%

EXAMPLE V-3

In 2 ml of ethanol is suspended 0.2 g of (R)-1-cyclopropyl-8-difluoromethoxy-7-(1-methyl-2,3-dihydro-1H-5-isoindolyl)-4-oxo-1,4-dihydro-3-quinolinecarboxylic acid methanesulfonate monohydrate and the suspension is stirred at room temperature for 15 hours, and then subjected to collection by filtration to obtain 0.14 g of (R)-1-cyclopropyl-8-difluoromethoxy-7-(1-methyl-2,3-dihydro-1H-5-isoindolyl)-4-oxo-1,4-dihydro-3-quinolinecarboxylic acid methanesulfonate.

The physical property values of the compound obtained above were identical with those of the compound obtained in Example V-2.

Water content: 0.33%

Reference Example V-1

In 10 ml of 50% water-containing ethanol is suspended 0.5 g of (R)-1-cyclopropyl-8-difluoromethoxy-7-(1-methyl-2,3-dihydro-1H-5-isoindolyl)-4-oxo-1,4-dihydro-3-quinolinecarboxylic acid and the suspension is warmed to 50° C., after which 0.14 g of phosphoric acid is added to the warmed suspension to form a uniform solution. Subsequently, the solution is stirred at the same temperature for 10 minutes and then subjected to filtration. The filtrate is cooled to room temperature and then the crystals deposited are collected by filtration to obtain 0.32 g of (R)-1-cyclopropyl-8-difluoromethoxy-7-(1-methyl-2,3-dihydro-1H-5-isoindolyl)-4-oxo-1,4-dihydro-3-quinoline-carboxylic acid phosphate.

IR (KBr) cm$^{-1}$: $v_{C=O}$ 1722, 1616

NMR (TFA-d) δvalue: 1.1–2.1(7H, m), 4.5–5.6(4H, m), 6.20(1H, t, J=75 Hz), 7.4–8.0(3H, m), 8.14(1H, d, J=10 Hz), 8.80(1H, d, J=10 Hz), 9.65(1H, s)

Reference Example V-2

In 8.2 ml of 40% water-containing ethanol is suspended 0.7 g of (R)-1-cyclopropyl-8-difluoromethoxy-7-(1-methyl-2,3-dihydro-1H-5-isoindolyl)-4-oxo-1,4-dihydro-3-quinolinecarboxylic acid and then 0.16 g of L-lactic acid is added thereto, after which the resulting mixture is warmed to 50° C. to form a uniform solution. Subsequently, the solution is subjected to filtration at the same temperature and the filtrate is thereafter concentrated, and the crystals deposited are collected by filtration to obtain 0.57 g of (R)-1-cyclopropyl-8-difluoromethoxy-7-(1-methyl-2,3-dihydro-1H-5-isoindolyl)-4-oxo-1,4-dihydro-3-quinolinecarboxylic acid L-lactate.

IR (KBr) cm$^{-1}$: $v_{C=O}$ 1723, 1616

NMR (TFA-d) δvalue: 1.2–2.1(10H, m), 4.4–5.6(5H, m), 6.19(1H, t, J=72 Hz), 7.5–8.0(3H, m), 8.14(1H, d, J=10 Hz), 8.79(1H, d, J=10 Hz), 9.64(1H, s)

Reference Example V-3

In 9.4 ml of 25% water-containing ethanol is suspended 1.2 g of (R)-1-cyclopropyl-8-difluoromethoxy-7-(1-methyl-2,3-dihydro-1H-5-isoindolyl)-4-oxo-1,4-dihydro-3-quinolinecarboxylic acid, and 2.57 ml of 1 mole/liter aqueous sodium hydroxide solution is added thereto, after which the resulting mixture is exposed to ultrasonic wave for 1 hour to form a uniform solution. Subsequently, the reaction mixture is washed twice with chloroform, and concentrated, and the crystals deposited are collected by filtration to obtain 0.49 g of sodium (R)-1-cyclopropyl-8-difluoromethoxy-7-(1-methyl-2,3-dihydro-1H-5-isoindolyl)-4-oxo-1,4-dihydro-3-quinolinecarboxylate.

IR (KBr) cm$^{-1}$: vC=O 1636

NMR (TFA-d) δvalue: 1.2–2.1(7H, m), 4.6–5.6(4H, m), 6.20(1H, t, J=72 Hz), 7.5–8.0(3H, m), 8.17(1H, d, J=10 Hz), 8.79(1H, d, J=10 Hz), 9.66(1H, s)

Reference Example V-4

In 42 ml of 50% water-containing ethanol is suspended 0.2 g of (R)-1-cyclopropyl-8-difluoromethoxy-7-(1-methyl-2,3-dihydro-1H-5-isoindolyl)-4-oxo-1,4-dihydro-3-quinolinecarboxylic acid and 0.11 g of citric acid is then added thereto, after which the resulting mixture is warmed to 65° C. to form a uniform solution. Subsequently, the solution is filtered at the same temperature and the filtrate is concentrated, after which the crystals deposited are collected by filtration to obtain 0.24 g of (R)-1-cyclopropyl-8-difluoromethoxy-7-(1-methyl-2,3-dihydro-1H-5-isoindolyl)-4-oxo-1,4-dihydro-3-quinolinecarboxylic acid citrate.

IR (KBr) cm$^{-1}$: $v_{C=O}$ 1724, 1616

Reference Example V-5

In 0.75 ml of acetic acid is suspended 0.5 g of (R)-1-cyclopropyl-8-difluoromethoxy-7-(1-methyl-2, 3-dihydro- 1H-5-isoindolyl)-4-oxo-1, 4-dihydro-3-quinolinecarboxylic acid and the suspension is warmed to 80° C. to form a uniform solution. Subsequently, the solution is filtered at the same temperature and then 2.5 ml of ethanol is added to the filtrate, after which the crystals deposited are collected by filtration to obtain 0.24 g of (R)-1-cyclopropyl-8-difluoromethoxy-7-(1-methyl-2,3-dihydro-1H-5-isoindolyl)-4-oxo-1,4-dihydro-3-quinolinecarboxylic acid acetate.

IR (KBr) cm$^{-1}$: $v_{C=O}$ 1723, 1622

NMR (TFA-d) δvalue: 1.2–2.1(7H, m), 2.28(3H, s), 4.7–5.6(4H, m), 6.20(1H, t, J=74 Hz), 7.5–8.0(3H, m), 8.14(1H, d, J=10 Hz), 8.80(1H, d, J=10 Hz), 9.64(1H, s)

Reference Example V-6

In 20 ml of 50% water-containing ethanol is suspended 1.0 g of (R)-1-cyclopropyl-8-difluoromethoxy-7-(1-methyl-2,3-dihydro-1H-5-isoindolyl)-4-oxo-1,4-dihydro-3-quinolinecarboxylic acid and the suspension is then warmed to 50° C., after which 0.41 ml of 6 moles/liter hydrochloric acid is added thereto to form a uniform solution. Subsequently, the solution is stirred at the same temperature for 10 minutes and then filtered. The filtrate is cooled to room temperature and the crystals deposited are thereafter collected by filtration to obtain 0.56 g of (R)-1-cyclopropyl-8-difluoromethoxy-7-(1-methyl-2,3-dihydro-1H-5-isoindolyl)-4-oxo-1,4-dihydro-3-quinolinecarboxylic acid hydrochloride.

IR (KBr) cm$^{-1}$: $v_{C=O}$ 1722, 1616

NMR (TFA-d) δvalue: 1.2–2.1(7H, m), 4.5–5.6(4H, m), 6.21(1H, t, J=73 Hz), 7.5–8.0(3H, m), 8.15(1H, d, J=10 Hz), 8.78(1H, d, J=10 Hz), 9.65(1H, s)

Reference Example V-7

In 12 ml of 20% water-containing ethanol is suspended 0.6 g of (R)-1-cyclopropyl-8-difluoromethoxy-7-(1-methyl-2,3-dihydro-1H-5-isoindolyl)-4-oxo-1,4-dihydro-3-quinolinecarboxylic acid and 74 mg of magnesium ethoxide is then added thereto, after which the resulting mixture is heated under reflux for 2 hours. Subsequently, the reaction mixture is cooled to room temperature and thereafter the crystals are collected by filtration to obtain 0.55 g of magnesium salt of (R)-1-cyclopropyl-8-difluoromethoxy-7-(1-methyl-2,3-dihydro-1H-5-isoindolyl)-4-oxo-1,4-dihydro-3-quinolinecarboxylic acid.

IR (KBr) cm$^{-1}$: $v_{C=O}$ 1612

NMR (TFA-d) δvalue: 1.1–2.1(7H, m), 4.5–5.6(4H, m), 6.20(1H, t, J=73 Hz), 7.5–8.0(3H, m), 8.12(1H, d, J=10 Hz), 8.78(1H, d, J=10 Hz), 9.65(1H, s)

Reference Example V-8

In 10 ml of 50% water-containing ethanol is suspended 0.5 g of (R)-1-cyclopropyl-8-difluoromethoxy-7-(1-methyl-2,3-dihydro-1H-5-isoindolyl)-4-oxo-1,4-dihydro-3-quinolinecarboxylic acid and the suspension is then warmed to 50° C., after which 0.12 g of sulfuric acid is added thereto to form a uniform solution. Subsequently, the solution is stirred at the same temperature for 10 minutes and then filtered. The filtrate is cooled to room temperature and thereafter the crystals deposited are collected by filtration to obtain 0.34 g of (R)-1-cyclopropyl-8-difluoromethoxy-7-(1-methyl-2,3-dihydro-1H-5-isoindolyl)-4-oxo-1,4-dihydro-3-quinolinecarboxylic acid sulfate.

IR (KBr) cm$^{-1}$: $v_{C=O}$ 1724, 1615

NMR (TFA-d) δvalue: 1.2–2.1(7H, m), 4.6–5.6(4H, m), 6.20(1H, t, J=73 Hz), 7.5–8.0(3H, m), 8.12(1H, d, J=10 Hz), 8.80(1H, d, J=10 Hz), 9.65(1H, s)

Preparation Example V-1

380.4 g of (R)-1-cyclopropyl-8-difluoromethoxy-7-(1-methyl-2,3-dihydro-1H-5-isoindolyl)-4-oxo-1,4-dihydro-3-quinolinecarboxylic acid methanesulfonate monohydrate, 83.1 g of lactose, 36 g of corn starch and 27 g of carboxymethyl starch sodium (Primojel, Matsutani Kagaku) are mixed, and the mixture is thereafter introduced into a kneader (small size bench kneader, Koike Tekko) and then kneaded while 180 g of a 6% aqueous hydroxypropyl cellulose solution (HPC-L, Nippon Soda) is gradually added. The kneaded product is subjected to size reduction by a power mill (PS-04S, Dalton, 2-mm herringbone screen) and then dried by blowing air at 40° C. overnight. After the drying, the product is subjected to size reduction by a power mill (20-mesh square screen), and thereafter, 2.7 g of magnesium stearate is added thereto and mixed therewith to prepare a powder for tableting. This powder is tableted by a rotary type tablet machine (HP-18, Hata Tekko) using a punch having a diameter of 7.5 mm so that the weight of one tablet becomes 180 mg to obtain tablets each containing 100 mg of (R)-1-cyclopropyl-8-difluoromethoxy-7-(1-methyl-2,3-dihydro-1H-5-isoindolyl)-4-oxo-1,4-dihydro-3-quinolinecarboxylic acid (as free base). This tablet is subjected to film coating in an aqueous system by conventional procedure (4 mg of hydroxypropylmethyl cellulose (TC-5), 0.8 mg of Macrogol 6000, 0.4 mg of titanium oxide and 0.4 mg of talc per tablet) to obtain a film-coated tablet.

Preparation Example V-2

Into 958 g of water for injection is introduced 6.338 g of (R)-1-cyclopropyl-8-difluoromethoxy-7-(1-methyl-2,3-dihydro-1H-5-isoindolyl)-4-oxo-1,4-dihydro-3-quinolinecarboxylic acid methanesulfonate monohydrate while stirring to dissolve the latter in the former. To the solution are added 0.62 ml of 0.1 mole/liter methanesulfonic acid and 50 g of D-mannitol and the resulting mixture is further stirred. After the complete dissolution, the solution is filtered through a 0.22-μm membrane filter. This filtrate is charged into vials in a proportion of 100 ml per vial and each of the vials is stopped with a rubber compound stopper and an aluminum cap and thereafter subjected to steam sterilization (121° C., 20 minutes) to obtain injections, each vial containing 500 mg of (R)-1-cyclopropyl-8-difluoromethoxy-7-(1-methyl-2,3-dihydro-1H-5-isoindolyl)-4-oxo-1,4-dihydro-3-quinolinecarboxylic acid (as free base).

INDUSTRIAL APPLICABILITY

The production process of this invention is useful as a process for the industrial production of a 7-isoindoline-quinolonecarboxylic acid derivative useful as an antibacterial agent, particularly T-3811 and isoindoline-5-boronic acid derivatives, 1-alkylisoindoline-5-boronic acid derivatives, 1-alkyl-5-halogenoisoindoline derivatives and 7-bromo-quinolonecarboxylic acid derivatives which are intermediates for T-3811.

Moreover, t-3811 methanesulfonate is remarkably high in solubility at a physiologically acceptable pH and further t-3811 methanesulfonate monohydrate has no polymorphism and is good in stability against humidity and hence useful as the starting material for a composition comprising t-3811 as an active ingredient, particularly for a t-3811 preparation.

What is claimed is:

1. A process for producing a 7- isoindolinequinolonecarboxylic acid derivative or its salt, represented by the general formula [1]:

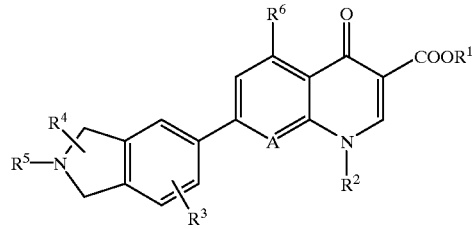

[1]

wherein $R^1$ represents a hydrogen atom or a carboxyl-protecting group; $R^2$ represents a substituted or unsubstituted alkyl, alkenyl, cycloalkyl, aryl or heterocyclic group; $R^3$ represents at least one group selected from hydrogen atom, halogen atoms, substituted or unsubstituted alkyl, alkenyl, cycloalkyl, aryl, alkoxy or alkylthio groups, nitro group, cyano group, acyl groups, protected or unprotected hydroxyl groups or protected or unprotected or substituted or unsubstituted amino groups; $R^4$ represents at least one group selected from hydrogen atom, halogen atom, substituted or unsubstituted alkyl, alkenyl, cycloalkyl, aralkyl, aryl, alkoxy or alkylthio groups, protected or unprotected hydroxyl or imino groups, protected or unprotected or substituted or unsubstituted amino groups, alkylidene groups, oxo group or groups each forming a cycloalkane ring together with the carbon atom to which $R^4$ bonds; $R^5$ represents a hydrogen atom, an amino-protecting group, a substituted or unsubstituted alkyl, cycloalkyl, alkylsulfonyl, arylsulfonyl, acyl or aryl group; $R^6$ represents a hydrogen atom, a halogen atom, a substituted or unsubstituted alkyl, alkoxy or alkylthio group, a protected or unprotected hydroxyl or amino group or a nitro group; and A represents CH or C—$R^7$ in which $R^7$ represents a halogen atom, a substituted or unsubstituted alkyl, alkoxy or alkylthio group or a protected or unprotected hydroxyl group, comprising:

reacting, in the presence of metallic palladium an isoindoline-5-boronic acid derivative represented by the following general formula [2] or its salt:

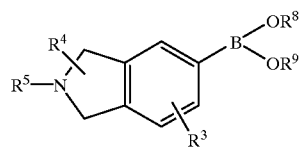

[2]

wherein $R^3$, $R^4$ and $R^5$ have the same meanings as mentioned above; and $R^8$ and $R^9$ represent hydrogen atoms or lower alkyl groups or form a ring comprising the boron atom when taken together, with a 7-leaving group-substituted quinolonecarboxylic acid represented by the following general formula [3] or its salt:

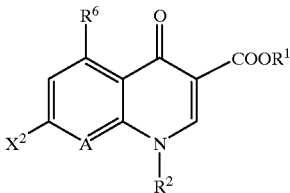

[3]

wherein $R^1$, $R^2$, $R^6$ and A have the same meanings as mentioned above; and $X^2$ represents a leaving group.

2. A process for producing a 7- isoindolinequinolonecarboxylic acid derivative or its salt according to claim 1, wherein the compound represented by the general formula [2] or its salt is a compound represented by the general formula [2b] or its salt:

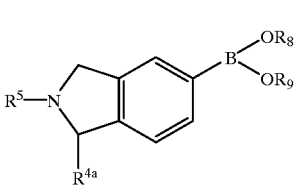

[2b]

wherein $R^{4a}$ represents an alkyl group; $R^5$ represents a hydrogen atom, an amino-protecting group, a substituted or unsubstituted alkyl, cycloalkyl, alkylsulfonyl, arylsulfonyl, acyl or aryl group; and $R^8$ and $R^9$ represent hydrogen atoms or lower alkyl groups or form a ring comprising the boron atom when taken together, obtained by reacting a phenylalkylamine derivative represented by the general formula [10] or its salt:

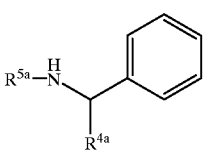

[10]

wherein $R^{4a}$ has the same meaning as mentioned above; and $R^{5a}$ represents an amino-protecting group, a substituted or unsubstituted alkyl, cycloalkyl, alkylsulfonyl, arylsulfonyl, acyl or aryl group, with carbon dioxide, a halogenated formic acid ester or a carbonic acid ester in the presence of a base to form a 2-aminoalkylbenzoic acid derivative represented by the general formula [9] or its salt:

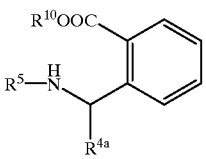

[9]

wherein $R^{4a}$ and $R^5$ have the same meanings as mentioned above; and $R^{10}$ represents a hydrogen atom or a carboxyl-protecting group, subsequently subjecting the 2-aminoalkylbenzoic acid derivative or its salt to halogenation reaction to obtain a 2-aminoalkyl-5-halogenobenzoic acid derivative represented by the general formula [8] or its salt:

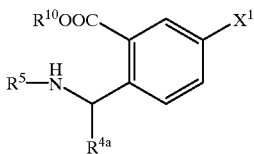

[8]

wherein $R^{4a}$, $R^5$ and $R^{10}$ have the same meanings as mentioned above; and $X^1$ represents a halogen atom, subsequently subjecting the 2-aminoalkyl-5-halogenobenzoic acid derivative or is salt to reduction reaction to obtain a 2-aminoalkyl-5-halogenobenzyl alcohol derivative represented by the following general formula [6] or its salt:

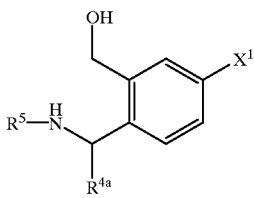

[6]

wherein $R^{4a}$, $R^5$ and $X^1$ have the same meanings as mentioned above, and thereafter subjecting the 2-aminoalkyl-5-halogenobenzyl alcohol derivative or its salt to ring-closing reaction to obtain a 1-alkyl-5-halogenoisoindoline derivative represented by the general formula [4a] or its salt:

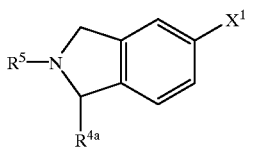

[4a]

wherein $R^{4a}$, $R^5$ and $X^1$ have the same meanings as mentioned above and then subjecting the 1-alkyl-5-halogenoisoindoline derivative or its salt to borodation, the compound represented by the general formula [3] or its salt is a compound represented by the general formula [3b] or its salt:

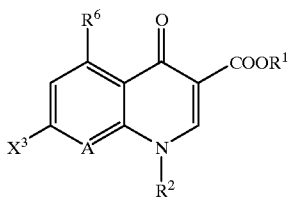

[3b]

wherein $R^1$, $R^2$, $R^6$ and A have the same meanings as mentioned above and $X^3$ represents a halogen atom, the compound represented by the general formula [1a] or its salt is

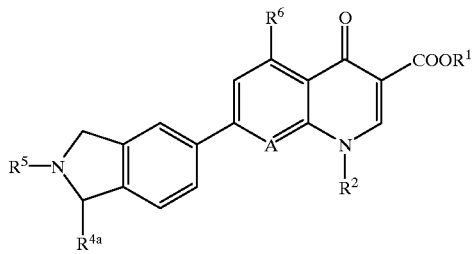

[1a]

wherein $R^{4a}$, $R^1$, $R^2$, $R^5$, $R^6$ and A have the same meanings as mentioned above.

3. A process for producing a 7-isoindolinequinolonecarboxylic acid derivative or its salt according to claim 1, wherein the compound represented by the general formula [2] or its salt is a compound represented by the general formula [2b] or its salt:

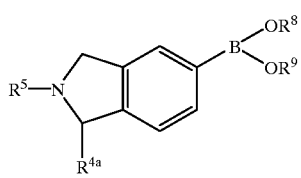

[2b]

wherein $R^{4a}$ represents an alkyl group; $R^5$ represents a hydrogen atom, an amino-protecting group, a substituted or unsubstituted alkyl, cycloalkyl, alkylsulfonyl, arylsulfonyl, acyl or aryl group; and $R^8$ and $R^9$ represent hydrogen atoms or lower alkyl groups or form a ring comprising the boron atom when taken together, obtained by reacting a phenylalkylamine derivative represented by the general formula [10] or its salt:

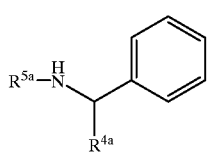

[10]

wherein $R^{4a}$ has the same meaning as mentioned above; and $R^{5a}$ represents an amino-protecting group, a substituted or unsubstituted alkyl, cycloalkyl, alkylsulfonyl, arylsulfonyl, acyl or aryl group, with carbon dioxide, a halogenated formic acid ester or a carbonic acid ester in the presence of a base, to obtain a 2-aminoalkylbenzoic acid derivative represented by the general formula [9] or its salt:

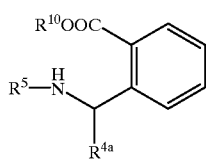

[9]

wherein $R^{4a}$ and $R^5$ have the same meanings as mentioned above; and $R^{10}$ represents a hydrogen atom or a carboxyl-protecting group, subsequently subjecting the 2-aminoalkylbenzoic acid derivative or its salt to halogenation reaction to obtain a 2-aminoalkyl-5-halogenobenzoic acid derivative represented by the general formula [8] or its salt:

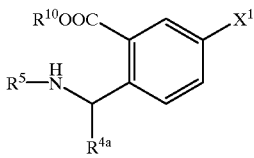

[8]

wherein $R^{4a}$, $R^5$ and $R^{10}$ have the same meanings as mentioned above; and $X^1$ represents a halogen atom, subsequently subjecting the 2-aminoalkyl-5-halogenobenzoic acid derivative or is salt to ring-closing reaction to obtain a 1-alkyl-3-oxo-5-halogenoisoindoline derivative represented by the general formula [7] or its salt:

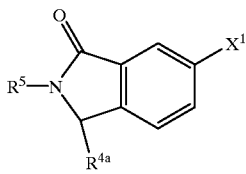

[7]

wherein $R^{4a}$, $R^5$ and $X^1$ have the same meanings as mentioned above, subsequently subjecting the 1-alkyl-3-oxo-5-halogenoisoindoline derivative or its salt to reduction reaction to obtain a 1-alkyl-5-halogenoisoindoline derivative represented by the general formula [4a] or its salt:

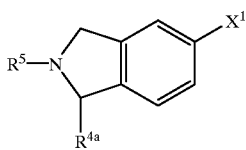

[4a]

wherein $R^{4a}$, $R^5$ and $X^1$ have the same meanings as mentioned above, and then subjecting the 1-alkyl-5-halogenoisoindoline derivative or its salt to borodation,
the compound represented by the general formula [3] or its salt is a compound represented by the general formula [3b] or its salt:

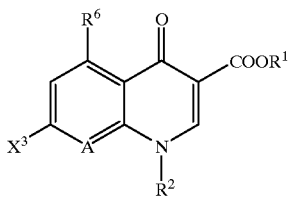

[3b]

wherein $R^1$, $R^2$, $R^6$ and A have the same meanings as mentioned above and $X^3$ represents a halogen atom, and
the compound represented by the general formula [1] or its salt is a compound represented by the general formula [1a] or its salt:

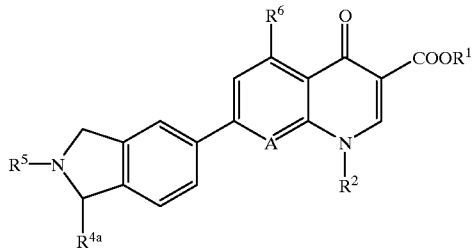

[1a]

wherein $R^{4a}$, $R^1$, $R^2$, $R^5$, $R^6$ and A have the same meanings as mentioned above.

4. A process for producing a 7-isoindoline-quinolonecarboxylic acid derivative or its salt according to claim 1, wherein
the compound represented by the general formula [2] or its salt is a compound represented by the general formula [2b] or its salt:

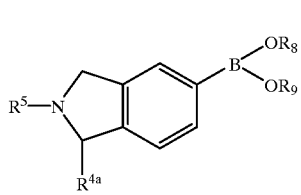

[2b]

wherein $R^{4a}$ represents an alkyl group; $R^5$ represents a hydrogen atom, an amino-protecting group, a substituted or unsubstituted alkyl, cycloalkyl, alkylsulfonyl, arylsulfonyl, acyl or aryl group; and $R^8$ and $R^9$ represent hydrogen atoms or lower alkyl groups or form a ring comprising the boron atom when taken together, obtained by preparing a compound represented by the general formula [4a] or its salt

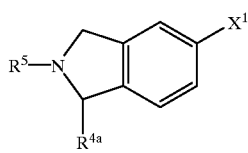

[4a]

wherein $R^{4a}$ represents an alkyl group; $R^5$ represents a hydrogen atom, an amino-protecting group, a substituted or unsubstituted alkyl, cycloalkyl, alkylsulfonyl, arylsulfonyl, acyl or aryl group; and $X^1$ represents a halogen atom, obtained by reacting a 4-halogenobenzylamine derivative represented by the general formula [12] or its salt:

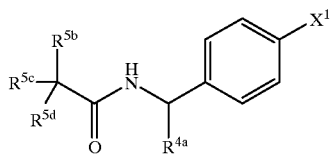

[12]

wherein $R^{4a}$ and $X^1$ have the same meanings as mentioned above; and $R^{5b}$, $R^{5c}$ and $R^{5d}$ may be the same or different and each represents an alkyl group, with formaldehyde or its derivative in the presence of an aryllithium to obtain a 2-aminoalkyl-5-halogenobenzyl alcohol derivative represented by the general formula [6] or its salt;

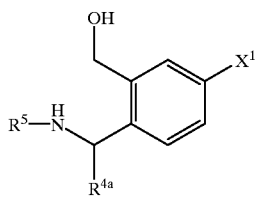

[6]

wherein $R^{4a}$, $R^5$ and $X^1$ have the same meanings as mentioned above, subsequently introducing a leaving group thereinto to obtain a 2-aminoalkyl-5-halogenobenzyl derivative represented by the general formula [1] or its salt:

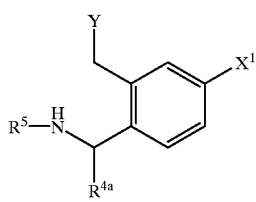

[11]

wherein $R^{4a}$, $R^5$ and $X^1$ have the same meanings as mentioned above; and Y represents a leaving group, and subsequently subjecting the 2-aminoalkyl-5-halogenobenzyl derivative to ring-closing reaction in the presence of a base, and subjecting the compound represented by the general formula [4a] or its salt to borodation, and the compound represented by the general formula [1] or its salt is a compound represented by the general formula [1a] or its salt:

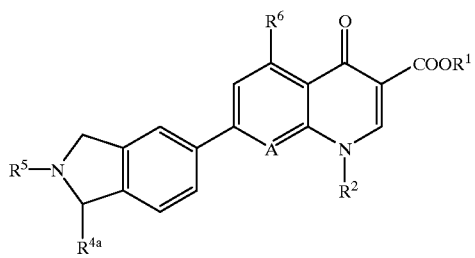

[1a]

wherein $R^{4a}$, $R^1$, $R^2$, $R^5$, $R^6$ and A have the same meanings as mentioned above.

5. A process for producing a 7-isoindolinequinolonecarboxylic acid derivative or its salt according to claim 1, wherein the compound represented by the general formula [3] or its salt is a compound represented by the general formula [3a] or its salt:

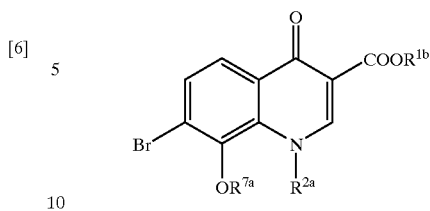

[3a]

wherein $R^{1b}$ represents a carboxyl-protecting group; $R^{2a}$ represents a substituted or unsubstituted alkyl, cycloalkyl, aryl or heterocyclic group; and $R^{7a}$ represents a substituted or unsubstituted alkyl group, obtained by reacting a 2,4-dibromo-3-hydroxybenzoic acid ester represented by the general formula [13] or its salt:

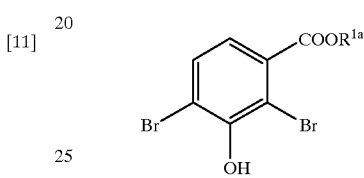

[13]

wherein $R^{1a}$ represents a carboxyl-protecting group, with a compound represented by the general formula [14]:

$$R^{7a}\text{—}X \qquad [14]$$

wherein $R^{7a}$ has the same meaning as mentioned above; and X represents a halogen atom, to obtain a 3-alkoxy-2,4-dibromobenzoic acid ester represented by the general formula [15] or its salt:

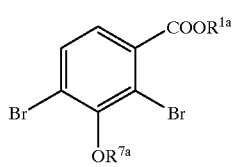

[15]

wherein $R^{1a}$ and $R^{7a}$ have the same meanings as mentioned above, subsequently subjecting the 3-alkoxy-2,4-dibromobenzoic acid ester to elimination reaction of the carboxyl-protecting group to obtain a 3-alkoxy-2,4-dibromobenzoic acid represented by the general formula [16] or its salt:

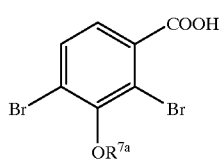

[16]

wherein $R^{7a}$ has the same meaning as mentioned above, subsequently subjecting the 3-alkoxy-2,4-dibromobenzoic acid to ketoesterification reaction to obtain a 3-alkoxy-2,4-dibromobenzoylacetic acid ester represented by the general formula [17] or its salt:

[17]

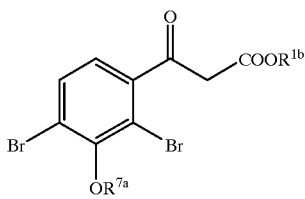

wherein $R^{1b}$ represents a carboxyl-protecting group; and $R^{7a}$ has the same meaning as mentioned above, subsequently reacting the 3-alkoxy-2,4-dibromobenzoylacetic acid ester with an orthoester or an acetal, then reacting the reaction product with a compound represented by the general formula [18] or its salt:

$R^{2a}$—NH    [18]

wherein $R^{2a}$ has the same meaning as mentioned above, to obtain a 2-(3-alkoxy-2,4-dibromobenzoyl)-3-substituted aminoacrylic acid ester represented by the general formula [19] or its salt:

[19]

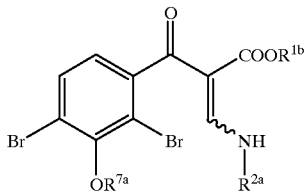

wherein $R^{1b}$, $R^{2a}$ and $R^{7a}$ have the same meanings as mentioned above, and thereafter subjecting the 2-(3-alkoxy-2,4-dibromobenzoyl)-3-substituted aminoacrylic acid ester to ring-closing reaction, and the compound represented by the general formula [1] or its salt is a compound represented by the general formula [1b] or its salt:

[1b]

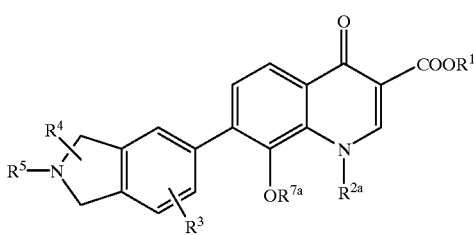

wherein $R^1$, $R^{2a}$, $R^3$, $R^4$, $R^5$ and $R^{7a}$ have the same meanings as mentioned above.

6. A process for producing a 7-isoindolinequinolonecarboxylic acid derivative or its salt according to claim 1, wherein $R^5$ represents a hydrogen atom, a substituted or unsubstituted alkyl, cycloalkyl, alkylsulfonyl, arylsulfonyl, acyl or aryl group.

7. (R)-1-Cyclopropyl-8-difluoromethoxy-7-(1-methyl-2,3-dihydro-1H-5-isoindolyl)-4-oxo-1,4-dihydro-3-quinolinecarboxylic acid methanesulfonate.

8. (R)-1-Cyclopropyl-8-difluoromethoxy-7-(1-methyl-2,3-dihydro-1H-5-isoindolyl)-4-oxo-1,4-dihydro-3-quinolinecarboxylic acid methanesulfonate monohydrate.

9. A composition comprising an active ingredient selected from the group consisting of (R)-1-cyclopropyl-8-difluoromethoxy-7-(1-methyl-2,3-dihydro-1H-5-isoindolyl)-4-oxo-1,4-dihydro-3-quinolinecarboxylic acid methanesulfonate and (R)-1-cyclopropyl-8-difluoromethoxy-7-(1-methyl-2,3-dihydro-1H-5-isoindolyl)-4-oxo-1,4-dihydro-3-quinolinecarboxylic acid methanesulfonate monohydrate, and an inactive ingredient.

10. The composition according to claim 9, wherein the inactive ingredient is a carrier acceptable as a preparation.

11. A process for producing a 7-isoindoline-quinolonecarboxylic acid derivative or its salt according to claim 1, wherein the compound represented by the general formula [2] or its salt is a compound represented by the general formula [2b] or its salt, the compound represented by the general formula [3] or its salt is a compound represented by the general formula [3b] or its salt, and the compound represented by the general formula or its salt is a compound represented by the general formula [1a] or its salt.

12. A process for producing a 7-isoindoline-quinolonecarboxylic acid derivative or its salt according to claim 1, wherein the compound represented by the general formula [2] or its salt is a compound represented by the general formula [2b] or its salt, the compound represented by the general formula [3] or its salt is a compound represented by the general formula [3b] or its salt, and the compound represented by the general formula [1] or its salt is a compound represented by the general formula [1a] or its salt.

13. A process for producing a 7-isoindoline-quinolonecarboxylic acid derivative or its salt according to claim 1, wherein the compound represented by the general formula [2] or its salt is a compound represented by the general formula [2b] or its salt obtained by preparing a compound represented by the general formula [4a] or its salt and subjecting the compound represented by the general formula [4a] or its salt to borodation, and the compound represented by the general formula [1] or its salt is a compound represented by the general formula [1a] or its salt.

14. A process for producing a 7-isoindoline-quinolonecarboxylic acid derivative or its salt according to claim 1, wherein the compound represented by the general formula [3] or its salt is a compound represented by the general formula [3a] or its salt, and the compound represented by the general formula [1] or its salt is a compound represented by the general formula [1b] or its salt.

* * * * *